(12) United States Patent
Peyronel et al.

(10) Patent No.: US 7,902,219 B2
(45) Date of Patent: Mar. 8, 2011

(54) 2-BENZOYLIMIDAZOPYRIDINE DERIVATIVES, PREPARATION AND THERAPEUTIC USE THEREOF

(75) Inventors: Jean-Francois Peyronel, Antony (FR); Youssef El-Ahmad, Antony (FR)

(73) Assignee: Sanofi-Aventis, Paris (FR)

( * ) Notice: Subject to any disclaimer, the term of this patent is extended or adjusted under 35 U.S.C. 154(b) by 28 days.

(21) Appl. No.: 12/336,989

(22) Filed: Dec. 17, 2008

(65) Prior Publication Data

US 2009/0143420 A1 Jun. 4, 2009

Related U.S. Application Data

(63) Continuation of application No. PCT/FR2007/001123, filed on Jul. 3, 2007.

(30) Foreign Application Priority Data

Jul. 3, 2006 (FR) .................................... 06 06010

(51) Int. Cl.
*A61K 31/437* (2006.01)
*C07D 471/04* (2006.01)

(52) U.S. Cl. ........................................ 514/300; 546/121
(58) Field of Classification Search .................. 546/121; 514/300

See application file for complete search history.

(56) References Cited

U.S. PATENT DOCUMENTS

2004/0204409 A1  10/2004 Ando et al.

FOREIGN PATENT DOCUMENTS

| FR | 2638161 | 4/1990 |
|---|---|---|
| WO | WO 01/74813 | 10/2001 |
| WO | WO 02/080911 | 10/2002 |
| WO | WO 03/059884 | 7/2003 |
| WO | WO 2004/072050 | 8/2004 |
| WO | WO 2005/028444 | 3/2005 |
| WO | WO 2005/044793 | 5/2005 |
| WO | WO 2005/048948 | 6/2005 |
| WO | WO 2006/024834 | 3/2006 |
| WO | WO 2006/067445 | 6/2006 |
| WO | WO 2006/067446 | 6/2006 |

OTHER PUBLICATIONS

U.S. Appl. No. 12/336,998, filed Dec. 17, 2008, Peyronel, et al.
U.S. Appl. No. 12/337,007, filed Dec. 17, 2008, El-Ahmad, et al.
U.S. Appl. No. 12/337,018, filed Dec. 17, 2008, Peyronel, et al.
Basha, et. al., A Mild, General Method for Conversion of Esthers to Amides, Tetrahedron Letters, No. 48, pp. 4171-4174, (1977), Pergamon Press.
Blache, Y., et. al., Compared Reactivity of 3-, 5-, 6-, and 8-Aminoimidazo[1,2-a]Pyridines in Combes Reaction: Access to Imidiazonaphthyridines and Dipyrido[1,2-a: 3', 2'-d]Imidazole, Heterocycles, vol. 38, No. 7, (1994) pp. 1527-1532.
Grassy, G., et. al., Inhibitory Effects on Platelet Aggregation and Cyclic AMP Phosphodiesterase of Azaindolizine-Type Compounds, Chemometrics and Intelligent Systems, vol. 20, (1993), pp. 71-84.
Kluger, R., et. al., Phosphoenolpyruvamides. Amide-Phosphate Interactions in Analogues of Phosphoenolpyruvate, J. Am. Chem. Soc. (1984), vol. 106, pp. 4017-4020.
Levin, J. I., et. al., An Alternative Procedure for the Aluminium-Mediated Conversion of Esters to Amides, Synthetic Communications, vol. 12, No. 13, pp. 989-993, (1983).
Lombardino, J. G., et. al., Preparation and New Reactions of Imidazo[1,2-a]Pyridines, J. Org. Chem., (1965), vol. 30, No. 7, pp. 2403-2407.
Nahm, S., et. al., N-Methoxy-N-Methylamides as Effective Acylating Agents, Tetrahedron Letters, vol. 22, No. 39, pp. 3815-3818, (1981).
Schmitt, M., et. al., Imidazo[1,2-b]Pyridazines, XXII Some 5-Deaza Analogues. Syntheses of Some 2-Aryl-6-(Chloro, Methoxy, or Unsubstituted)-3-(Variously Substituted)Imidazo[1,2-a]Pyridines, and Their Affinity for Central and Mitochondrial Benzodiazepine Receptors, Aust. J. Chem. (1997), vol. 50, pp. 719-725.
Theuns, J., et. al., A Novel NR4A2 Promoter Variation Associated with Parkinson's Disease Alters Gene Expression, Neurobiology of Aging, vol. 25, (2004-2007), pp. S85.
Wang, Z., et. al., Structure and Function of Nurr1 Identifies a Class of Ligand-Independent Nuclear Receptors, Nature vol. 423, 555-560, (2003).

*Primary Examiner* — Patricia L Morris
(74) *Attorney, Agent, or Firm* — Jiang Lin

(57) ABSTRACT

The present invention is related to a compound of formula (I)

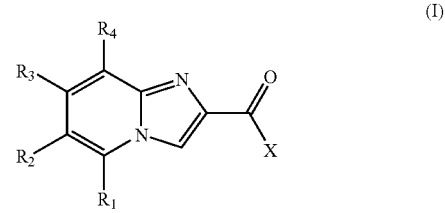

(I)

wherein R1, R2, R3, R4 and X are as defined herein, or an acid-addition salt thereof, its preparation and therapeutic use in the treatment or prevention of diseases involving the Nurr-1 nuclear receptors, also known as NR4A2, NOT, TINUR, RNR-1 and HZF3.

8 Claims, No Drawings

2-BENZOYLIMIDAZOPYRIDINE DERIVATIVES, PREPARATION AND THERAPEUTIC USE THEREOF

This application is a Continuation of International Application No. PCT/FR2007/001123, filed Jul. 3, 2007, which is incorporated herein by reference in its entirety.

FIELD OF THE INVENTION

The present invention relates to imidazo[1,2-a]pyridine-2-carboxamide derivatives, to their preparation and to their therapeutic use in the treatment or prevention of diseases involving the Nurr-1 nuclear receptors, also known as NR4A2, NOT, TINUR, RNR-1 and HZF3.

SUMMARY OF THE INVENTION

One subject of the present invention is compounds corresponding to the formula (I):

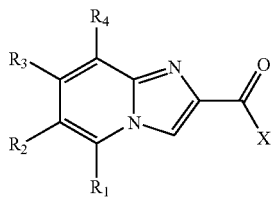

(I)

in which:
X represents:
  a phenyl group optionally substituted with one or more atoms or groups chosen, independently of each other, from the following atoms or groups: halogen, $(C_1\text{-}C_6)$alkoxy, $(C_1\text{-}C_6)$alkyl, $(C_3\text{-}C_7)$cycloalkyl$(C_1\text{-}C_6)$alkyl, $(C_3\text{-}C_7)$cycloalkyl$(C_1\text{-}C_6)$alkoxy, hydroxyl, amino and NRaRb;
$R_1$ represents a hydrogen atom, a halogen, a group $(C_1\text{-}C_6)$alkoxy, a group $(C_1\text{-}C_6)$alkyl, a group $(C_3\text{-}C_7)$cycloalkyl$(C_1\text{-}C_6)$alkyl, a group $(C_3\text{-}C_7)$cycloalkyl$(C_1\text{-}C_6)$alkoxy, a hydroxyl or an amino; the group $(C_1\text{-}C_6)$alkyl possibly being substituted with one or more of the following atoms or groups: halogens, hydroxyl, amino, $(C_1\text{-}C_6)$alkoxy, and the group $(C_1\text{-}C_6)$alkoxy possibly being substituted with one or more of the following atoms or groups: halogen, hydroxyl, amino, $(C_1\text{-}C_6)$alkoxy;
$R_2$ represents one of the following groups:
  a hydrogen atom,
  a group $(C_1\text{-}C_6)$alkyl optionally substituted with one or more atoms or groups chosen, independently of each other, from halogen, hydroxyl, amino and NRaRb,
  a group $(C_1\text{-}C_6)$alkoxy substituted with one or more atoms or groups chosen, independently of each other, from halogen, hydroxyl, amino and NRaRb,
  a group $(C_3\text{-}C_7)$cycloalkyl$(C_1\text{-}C_6)$alkyl,
  a group $(C_3\text{-}C_7)$cycloalkyl$(C_1\text{-}C_6)$alkoxy,
  a group $(C_2\text{-}C_6)$alkenyl,
  a group $(C_2\text{-}C_6)$alkynyl,
  a group —CO—$R_5$,
  a group —CO—NR$_6$R$_7$,
  a group —CO—O—$R_8$,
  a group —NR$_9$—CO—R$_{10}$,
  a group —NR$_{11}$R$_{12}$,
  a halogen atom,
  a cyano group,
  a phenyl group optionally substituted with one or more groups chosen, independently of each other, from the following atoms or groups: halogen, $(C_1\text{-}C_6)$alkoxy, $(C_1\text{-}C_6)$alkyl, $(C_3\text{-}C_7)$cycloalkyl$(C_1\text{-}C_6)$alkyl, $(C_3\text{-}C_7)$cycloalkyl$(C_1\text{-}C_6)$alkoxy, hydroxyl, amino, NRaRb, CO—$R_5$, the group $(C_1\text{-}C_6)$alkyl being optionally substituted with a hydroxyl group,
$R_3$ represents a hydrogen atom, a group $(C_1\text{-}C_6)$alkyl, a halogen atom or a hydroxyl group,
$R_4$ represents a hydrogen atom or a halogen atom,
$R_5$ represents a hydrogen atom or a group $(C_1\text{-}C_6)$alkyl,
$R_6$ and $R_7$, which may be identical or different, represent a hydrogen atom or a group $(C_1\text{-}C_6)$alkyl or form, with the nitrogen atom, a 4- to 7-membered ring optionally including another heteroatom chosen from N, O and S,
$R_8$ represents a group $(C_1\text{-}C_6)$alkyl,
$R_9$ and $R_{10}$, which may be identical or different, represent a hydrogen atom or a group $(C_1\text{-}C_6)$alkyl,
$R_{11}$ represents a group $(C_1\text{-}C_6)$alkyl,
$R_{12}$ represents a hydrogen or a group $(C_1\text{-}C_6)$alkyl,
$R_{11}$ and $R_{12}$ may form, with the nitrogen atom, a 4- to 7-membered ring optionally including another heteroatom chosen from N, O and S,
Ra represents a $(C_1\text{-}C_6)$alkyl
Rb represents a hydrogen or a $(C_1\text{-}C_6)$alkyl
at least one of the substituents $R_1$, $R_2$, $R_3$ and $R_4$ is not a hydrogen
with the exception of the compound for which X is a phenyl, $R_3$ is methyl and $R_1$, $R_2$ and $R_4$ are hydrogens; the compound for which X is a phenyl, $R_2$ is chlorine or methoxy and $R_1$, $R_3$ and $R_4$ are hydrogens; the compound for which X is a p-tolyl, $R_2$ is a methyl and $R_1$, $R_3$ and $R_4$ are hydrogens; the compound for which X is a p-chlorophenyl, $R_1$ is a chlorine, a methoxy or a methyl, and $R_2$, $R_3$ and $R_4$ are hydrogens; the compound for which X is a p-chlorophenyl, $R_2$ is a chlorine and $R_1$, $R_3$ and $R_4$ are hydrogens; the compound for which X is a p-chlorophenyl, $R_2$ is a methyl and $R_1$, $R_3$ and $R_4$ are hydrogens; the compound for which X is a p-chlorophenyl, $R_4$ is a methyl, and $R_1$, $R_2$ and $R_3$ are hydrogens; the compound for which X is a p-chlorophenyl, $R_3$ is a methyl and $R_1$, $R_2$ and $R_4$ are hydrogens; and the compound for which X is a p-chlorophenyl, $R_1$ and $R_3$ are methyls and $R_2$ and $R_4$ are hydrogens,
in the form of the base or of an acid-addition salt.

DETAILED DESCRIPTION OF THE INVENTION

The compounds of formula (I) may comprise one or more asymmetric carbon atoms. They may thus exist in the form of enantiomers or diastereoisomers. These enantiomers and diastereoisomers, and also mixtures thereof, including racemic mixtures, form part of the invention.

Among the compounds of formula (I) that are subjects of the invention, a first group of compounds is constituted of compounds for which:

R₁, R₃ and R₄ are hydrogen atoms in the form of the base or of an acid-addition salt.

Among the compounds of formula (I) that are subjects of the invention, a second group of compounds is constituted of compounds for which X is a phenyl group, in the form of the base or of an acid-addition salt.

The compounds of formula (I) may exist in the form of bases or of acid-addition salts. Such addition salts form part of the invention.

These salts may be prepared with pharmaceutically acceptable acids, but the salts of other acids that are useful, for example, for purifying or isolating the compounds of formula (I) also form part of the invention.

The compounds of formula (I) may also exist in the form of hydrates or solvates, i.e. in the form of associations or combinations with one or more water molecules or with a solvent. Such hydrates and solvates also form part of the invention.

In the context of the present invention, the following definitions apply:

a halogen atom: a fluorine, a chlorine, a bromine or an iodine;

a group $(C_1-C_6)$alkyl: a linear, branched or cyclic, saturated aliphatic group of 1 to 6 carbons. Examples that may be mentioned include methyl, ethyl, propyl, isopropyl, butyl, isobutyl, tert-butyl, cyclopropyl, cyclobutyl, cyclopentyl, cyclohexyl etc. groups;

a group $(C_2-C_6)$alkenyl: a linear or branched, monounsaturated or polyunsaturated aliphatic group of 2 to 6 carbons, comprising, for example, one or two ethylenic unsaturations;

a group $(C_1-C_6)$alkoxy: a radical —O-alkyl in which the alkyl group is as defined previously;

a group $(C_2-C_6)$alkynyl: a linear or branched, monounsaturated or polyunsaturated aliphatic group of 2 to 6 carbons, comprising, for example, one or two acetylenic unsaturations;

Among the compounds of formula (I) that are subjects of the invention, mention may be made especially of the following compounds:

(6-Methylimidazo[1,2-a]pyridin-2-yl)(phenyl)methanone and its hydrochloride (1:1)
Phenyl[6-(trifluoromethyl)imidazo[1,2-a]pyridin-2-yl] methanone and its hydrochloride (1:1)
Phenyl[6-(trifluoromethyl)imidazo[1,2-a]pyridin-2-yl] methanone
Phenyl[6-(trifluoromethyl)imidazo[1,2-a]pyridin-2-yl] methanone and its hydrobromide (1:1)
[6-(1-Hydroxy-1-methylethyl)imidazo[1,2-a]pyridin-2-yl] (phenyl)methanone and its hydrobromide (1:1)
[6-(Hydroxymethyl)imidazo[1,2-a]pyridin-2-yl] (phenyl) methanone
(6-Chloroimidazo[1,2-a]pyridin-2-yl)(2-methylphenyl) methanone
Phenyl(6-phenylimidazo[1,2-a]pyridin-2-yl)methanone
[5-(2-Methoxyethoxy)imidazo[1,2-a]pyridin-2-yl] (phenyl) methanone
N-(2-Benzoylimidazo[1,2-a]pyridin-6-yl)acetamide
(6-Isopropenylimidazo[1,2-a]pyridin-2-yl)(phenyl)methanone
2-Benzoyl-N,N-dimethylimidazo[1,2-a]pyridine-6-carboxamide
2-Benzoyl-N-methylimidazo[1,2-a]pyridine-6-carboxamide
Phenyl(6-vinylimidazo[1,2-a]pyridin-2-yl)methanone
(6-Ethylimidazo[1,2-a]pyridin-2-yl)(phenyl)methanone
(6-Fluoroimidazo[1,2-a]pyridin-2-yl)(phenyl)methanone
(6,8-Dichloroimidazo[1,2-a]pyridin-2-yl)(phenyl)methanone and its hydrochloride (1:1)
(7-Chloroimidazo[1,2-a]pyridin-2-yl)(phenyl)methanone
(6-Bromoimidazo[1,2-a]pyridin-2-yl)(phenyl)methanone
(5-Bromoimidazo[1,2-a]pyridin-2-yl)(phenyl)methanone
2-Benzoylimidazo[1,2-a]pyridine-6-carbonitrile
(5-Aminoimidazo[1,2-a]pyridin-2-yl)(phenyl)methanone
2-Benzoylimidazo[1,2-a]pyridine-6-carboxamide
(6-Iodolimidazo[1,2-a]pyridin-2-yl)(phenyl)methanone and its hydrobromide (1:1)
(7-Hydroxyimidazo[1,2-a]pyridin-2-yl)(phenyl)methanone and its hydrobromide (1:1)
(6,8-Difluoroimidazo[1,2-a]pyridin-2-yl)(phenyl)methanone and its hydrobromide (1:1)
2-benzoylimidazo[1,2-a]pyridine-6-carboxylate and its hydrobromide (1:1)
[6-(1-Ethoxypropyl)imidazo[1,2-a]pyridin-2-yl] (phenyl) methanone
1-(2-Benzoylimidazo[1,2-a]pyridin-6-yl)ethanone
2-Benzoylimidazo[1,2-a]pyridine-6-carbaldehyde
(6-Chloroimidazo[1,2-a]pyridin-2-yl)(3-methylphenyl) methanone
(6-Chloroimidazo[1,2-a]pyridin-2-yl)(4-methylphenyl) methanone
(6-Chloroimidazo[1,2-a]pyridin-2-yl)(3-fluorophenyl) methanone
(6-Chloroimidazo[1,2-a]pyridin-2-yl)(4-fluorophenyl) methanone
(6-Chloroimidazo[1,2-a]pyridin-2-yl)(3,5-difluorophenyl) methanone
(5-Methylimidazo[1,2-a]pyridin-2-yl)(phenyl)methanone
(6-Bromo-5-methylimidazo[1,2-a]pyridin-2-yl)(phenyl) methanone
(6-Chloroimidazo[1,2-a]pyridin-2-yl)(3-chlorophenyl) methanone
(6-Chloroimidazo[1,2-a]pyridin-2-yl)(3,4-difluorophenyl) methanone
[6-(Dimethylamino)imidazo[1,2-a]pyridin-2-yl](phenyl) methanone and its hexafluorophosphate (1:1)
{6-[3-(Hydroxymethyl)phenyl]imidazo[1,2-a]pyridin-2-yl} (phenyl)methanone
{6-[4-(Hydroxymethyl)phenyl]imidazo[1,2-a]pyridin-2-yl} (phenyl)methanone
{6-[2-(Hydroxymethyl)phenyl]imidazo[1,2-a]pyridin-2-yl} (phenyl)methanone
3-(2-Benzoylimidazo[1,2-a]pyridin-6-yl)benzaldehyde
(5,6-Dimethylimidazo[1,2-a]pyridin-2-yl)(phenyl)methanone.

In accordance with the invention, the compounds of general formula (I) may be prepared according to the process described in Scheme 1.

Scheme 1

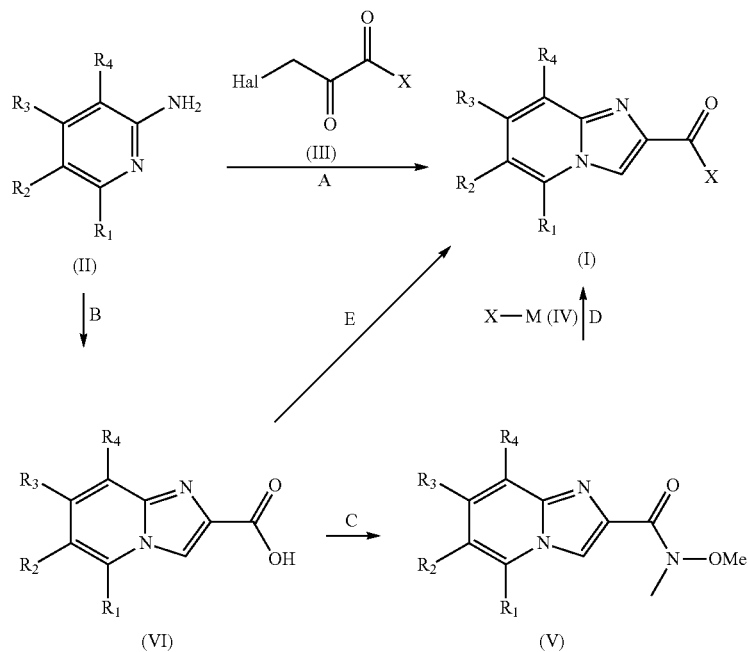

Route A consists in preparing the 2-aminopyridines of formula (II) according to the methods known to those skilled in the art and in forming the imidazo[1,2-a]pyridine ring by condensation with a 1-arylpropane-1,2-dione derivative (III) in which Hal represents a halogen, for example according to the method described by J-J. Bourguignon et al. in Aust. J. Chem. 1997, 50, 719-725.

The second synthetic route B-C-D consists in reacting an organometallic derivative of general formula (IV), in which X is defined as above and M represents a lithium atom or a group Mg-Hal, with a Weinreb amide of formula (V) in which the reactive functions are optionally protected, according to methods known to those skilled in the art, as described in Nahm, S.; Weinreb, S. M., Tetrahedron Letters (1981), 22(39), 3815-18 and in Sibi, M. P. Organic Preparations and Procedures Int. 1993, 25, 15-40. The Weinreb amide of formula (V) is obtained by coupling the acid derivative of formula (VI) or a reactive derivative thereof with an N,O-dialkylamine according to the methods described in the above references.

The coupling may be performed in the presence of a coupling agent such as CDI, EDCI, HATU or HBTU and of a base such as diisopropylethylamine, triethylamine or pyridine, in an inert solvent such as THF, DMF or dichloromethane. Alternatively, the N,O-dialkylamine may be reacted with an acid ester of formula (VI) in the presence of a catalyst such as trimethylaluminum (Levitt. J. I.; Turos. E.; Weinreb. S. M. Synth. Commun. 1982, 12, 989).

It is also possible, according to a third synthetic route (B-E), to react the organometallic derivative of general formula (IV) defined as above with an imidazo[1,2-a]pyridine-2-carboxylic acid of general formula (VI) in which $R_1$, $R_2$, $R_3$ and $R_4$ are as defined previously, or a salt or reactive derivative thereof such as ester, acid halide, anhydride or amide, according to the methods known to those skilled in the art, as described in J. March, Advanced Organic Chemistry (Wiley, 5th Ed. 2001) pp. 567 and 1213 or in the cited references. In this third synthetic route (B-E), a reactive derivative of the imidazo[1,2-a]pyridine-2-carboxylic acid of general formula (VI), such as a mixed anhydride (which may be generated in situ), may also be reacted with an organometallic derivative of general formula (IV) in which X is as defined above and M represents a boronic ester or acid group, in the presence of a palladium catalyst such as tetrakis(triphenylphosphine)palladium.

The products of formula (I) and the precursors thereof of formula (II) or (VI) may be subjected, if desired and if necessary, in order to obtain products of formula (I) or be converted into other products of formula (I), to one or more of the following transformation reactions, in any order:
a) a reaction for the esterification or amidation of an acid function,
b) a reaction for the hydrolysis of an ester function to an acid function,
c) a reaction for the transformation of a hydroxyl function into an alkoxy function,
d) a reaction for the oxidation of an alcohol function to an aldehyde or ketone function,
e) a reaction for the transformation of aldehyde or ketone functions into an alcohol function, via reduction or via reaction of an organometallic agent such as an organomagnesium reagent,
f) a reaction for the oxidation of an alkenyl group to an aldehyde or ketone function,
g) a reaction for the dehydration of a hydroxyalkyl group to an alkenyl group,
h) a reaction for the total or partial hydrogenation of an alkenyl or alkynyl group to an alkenyl or alkyl group,
i) a reaction for the catalytic coupling of a halo derivative and of an organometallic derivative such as stannyl or boryl to introduce an alkyl, alkenyl, alkynyl or aralkyl substituent,
j) a reaction for the reduction of a nitro group to an amino group, k) a reaction for the conversion of a primary or secondary amino group into a secondary or tertiary amino group via reductive amination or alkylation,
l) a reaction for the protection of reactive functions,
m) a reaction for the removal of the protecting groups that may be borne by the protected reactive functions,
n) a salification reaction with a mineral or organic acid or with a base, to obtain the corresponding salt,
o) a reaction for the resolution of racemic forms into enantiomers, said products of formula (I) thus obtained being, where appropriate, in any possible isomeric form: racemic mixtures, enantiomers and diastereoisomers.

In Scheme 1, the starting compounds and the reagents, when their mode of preparation is not described, are commercially available or are described in the literature, or else may be prepared according to methods that are described therein or that are known to those skilled in the art.

EXAMPLES

The examples that follow describe the preparation of certain compounds in accordance with the invention. These examples are not limiting, but serve merely to illustrate the present invention. The numbers of the illustrated compounds refer to those given in the table hereinbelow, which illustrates the chemical structures and spectroscopic characteristics of a number of compounds according to the invention.

Example 1

(6-Methylimidazo[1,2-a]pyridin-2-yl)(phenyl)methanone hydrochloride (1:1)

1.1 (6-Methylimidazo[1,2-a]pyridin-2-yl)(phenyl)methanone

To a solution of 454 mg of 3-bromo-1-phenylpropane-1,2-dione in 1 mL of methanol is added dropwise at 4° C. a solution of 179 mg of 2-amino-5-methylpyridine in 4 mL of methanol. The reaction mixture is stirred for 15 hours at 4° C. and then refluxed for 2 hours. After evaporating off the solvent under reduced pressure, the residue is taken up in dichloromethane and basified with normal sodium hydroxide solution. The basic aqueous phase is extracted with dichloromethane and the combined organic phases are washed with water and then with saturated sodium chloride solution, dried over magnesium sulfate, filtered and concentrated to dryness under reduced pressure. The residue is chromatographed on a cartridge of 20 g of silica, eluting with an 85/15 and then 65/35 mixture of cyclohexane and ethyl acetate. The fractions containing the expected product are combined and concentrated to dryness under reduced pressure to give 120 mg of (6-methylimidazo[1,2-a]pyridin-2-yl)phenylmethanone in the form of a beige-colored solid.

Mass spectrum (EI): m/z 236 (base peak): [M$^{+\cdot}$], m/z 208: M$^{+\cdot}$-[CO].

1.2 (6-Methylimidazo[1,2-a]pyridin-2-yl)(phenyl)methanone hydrochloride (1:1)

120 mg of (6-methylimidazo[1,2-a]pyridin-2-yl)phenylmethanone are taken up in 2 mL of ethanol and the solution is treated with 1.5 mL of a 4N solution of hydrogen chloride in dioxane and then with 2 mL of diethyl ether. The crystals obtained are filtered off and washed with diethyl ether, and then dried. 77 mg of (6-methylimidazo[1,2-a]pyridin-2-yl)phenylmethanone hydrochloride (1:1) are obtained in the form of a beige-colored solid.

Example 2

Phenyl[6-(trifluoromethyl)imidazo[1,2-a]pyridin-2-yl]methanone hydrochloride (1:1)

2.1 Phenyl[6-(trifluoromethyl)imidazo[1,2-a]pyridin-2-yl]methanone Hydrobromide (1:1)

To a solution of 0.324 g of 2-amino-5-trifluoromethylpyridine in 4 mL of DMF cooled to 4° C. is added dropwise a solution of 0.65 g of 3-bromo-1-phenylpropane-1,2-dione in 11 mL of DMF. The reaction mixture is stirred for 16 hours at 4° C. The precipitate is filtered off and washed with diethyl ether, and then dried. 0.32 g of phenyl[6-(trifluoromethyl)imidazo[1,2-a]pyridin-2-yl]methanone hydrobromide (1:1) is obtained in the form of a white solid.

$^1$H NMR spectrum (DMSO-d6, δ in ppm): 4.91 (d, J=14.5 Hz, 1H); 5.14 (d, J=14.5 Hz, 1H); 7.27 (m, 1H); 7.64 (t, J=7.5 Hz, 2H); 7.76 (t, J=7.5 Hz, 1H); 8.13 (d, J=8.0 Hz, 2H); 8.32 (m, 1H); 8.48 (m, 1H); 8.96 (s, 1H); 11.3 (s, 1H) (all the absorptions are broad).

Mass spectrum (EI): m/z 290: [M$^{+\cdot}$], m/z 203 (base peak): [M$^{+\cdot}$]-COPh IR spectrum (KBr): 3101; 2989; 1703; 1674; 1583; 1327; 1186; 1126; 1095; 1075; 934; 836; 723 and 692 cm$^{-1}$ 2.2 Phenyl[6-(trifluoromethyl)imidazo[1,2-a]pyridin-2-yl]methanone 0.32 g of phenyl[6-(trifluoromethyl)imidazo[1,2-a]pyridin-2-yl]methanone hydrobromide (1:1) is suspended in 10 mL of ethanol and the reaction medium is refluxed for 2 hours and then concentrated under reduced pressure. The residue is taken up in 10 mL of dichloromethane and 3 mL of aqueous normal sodium hydroxide solution. The organic phase is washed with water, dried over magnesium sulfate and concentrated to dryness under reduced pressure to give 220 mg of phenyl[6-(trifluoromethyl)imidazo[1,2-a]pyridin-2-yl]methanone in the form of a yellow solid.

Mass spectrum (EI): m/z 290: [M$^+$] (base peak), m/z 261: [M-CO]$^+$.

2.3 Phenyl[6-(trifluoromethyl)imidazo[1,2-a]pyridin-2-yl]methanone hydrochloride (1:1)

120 mg of phenyl[6-(trifluoromethyl)imidazo[1,2-a]pyridin-2-yl]methanone are taken up in 2 mL of methanol and the solution is treated with 2 mL of a 4N solution of hydrogen chloride in dioxane and then with 2 mL of diethyl ether. The solution is stirred for 16 hours at room temperature and then concentrated under reduced pressure. The solid obtained is dried to give 85 mg of phenyl[6-(trifluoromethyl)imidazo[1,2-a]pyridin-2-yl]methanone hydrochloride (1:1) in the form of a beige-colored solid.

Example 3

[6-(1-Hydroxy-1-methylethyl)imidazo[1,2-a]pyridin-2-yl] (phenyl)-methanone hydrobromide (1:1)

To a solution of 0.2 g of 2-(6-aminopyridin-3-yl)propan-2-ol in 10 mL of diglyme is added a solution of 0.358 g of 3-bromo-1-phenylpropane-1,2-dione in 5 mL of THF. The reaction mixture is stirred for 15 hours at 4° C. and then concentrated to dryness under reduced pressure. The residue is chromatographed on a column of silica, eluting with dichloromethane and then with a 98/2 mixture of dichloromethane and methanol. The fractions containing the expected product are combined and concentrated to dryness to give 60 mg of [6-(1-hydroxy-1-methylethyl)imidazo[1,2-a]pyridin-2-yl](phenyl)methanone hydrobromide (1:1) in the form of a straw-yellow solid.

Example 4

[6-(Hydroxymethyl)imidazo[1,2-a]pyridin-2-yl](phenyl)-methanone

To a solution of 0.12 g of 5-hydroxymethylpyridine in 5 mL of DME is added a solution of 0.7 g of 3-bromo-1-phenylpropane-1,2-dione in 5 mL of DME. The reaction mixture is stirred for 15 hours at 20° C. and then refluxed for 4 hours. The reaction medium is concentrated to dryness under reduced pressure. The residue is taken up in 50 mL of saturated sodium bicarbonate solution and 50 mL of ethyl acetate. The aqueous phase is extracted twice with 50 mL of ethyl acetate and the combined organic phases are washed with water, dried and concentrated to dryness. The residue is chromatographed on a cartridge of silica, eluting with a 90/10 mixture of dichloromethane and ethyl acetate. The fractions containing the expected product are combined and evaporated to dryness under reduced pressure to give 33 mg of [6-(hydroxymethyl)imidazo[1,2-a]pyridin-2-yl](phenyl)methanone in the form of a beige-colored solid.

Example 5

(6-Chloroimidazo[1,2-a]pyridin-2-yl)(2-methylphenyl)methanone

To a solution of 0.144 g of N-methoxy-N-methyl-6-chloroimidazo[1,2-a]pyridine-2-carboxamide in 3 mL of THF cooled to −4° C. is added dropwise a solution of 1.5 mL of a 2M solution of 2-methylphenylmagnesium chloride in ethyl ether. The reaction mixture is stirred for 3 hours at −4° C. 3 mL of 1N hydrochloric acid, 8 mL of water and 40 mL of ethyl acetate are added. After separation of the phases by settling, the organic phase is dried over magnesium sulfate, filtered, evaporated to dryness under reduced pressure, and then purified on a column of silica, eluting with a 90/10 mixture by volume of dichloromethane and ethyl acetate. The fractions containing the product are combined and concentrated to dryness under reduced pressure to give 0.034 g of (6-chloroimidazo[1,2-a]pyridin-2-yl)(2-methylphenyl)methanone in the form of a white solid.

Example 6

Phenyl(6-phenylimidazo[1,2-a]pyridin-2-yl)methanone 0.391 g of (6-bromoimidazo[1,2-a]pyridin-2-yl)(phenyl)methanone, 0.237 g of phenylboronic acid, 45 mg of tetrakis(triphenylphosphine)palladium, 4 mL of aqueous 2M sodium carbonate solution, 6 mL of acetonitrile and 6 mL of toluene are introduced into a 20 mL microwave tube. The mixture is stirred for 20 minutes in a microwave machine set at 150° C. After cooling, the organic phase is separated out, dried and evaporated. The residue is taken up in a mixture of dichloromethane and pentane. The solid is filtered off and then purified by trituration in methanol to give 0.16 g of phenyl(6-phenylimidazo[1,2-a]pyridin-2-yl)methanone in the form of an off-white solid.

Example 7

[5-(2-Methoxyethoxy)imidazo[1,2-a]pyridin-2-yl](phenyl)-methanone

To 800 μL of a 2.5 M solution of n-butyllithium in hexane are added 1.2 mL of dry 2-methoxyethanol, and the mixture is then allowed to warm to 20° C. 150 mg of (5-bromoimidazo[1,2-a]pyridin-2-yl)(phenyl)methanone are added and the mixture is heated for 20 minutes at 120° C. in a microwave machine. The cooled reaction mixture is taken up in 50 mL of water and 20 mL of ethyl acetate. The aqueous phase is re-extracted twice with 20 mL of ethyl acetate and the combined organic phases are washed with 50 mL of brine, dried over magnesium sulfate and concentrated. The residue is chromatographed on a column of silica, eluting with a 95/5 mixture of dichloromethane and methanol. The fractions containing the expected product are combined and concentrated to dryness under reduced pressure to give, after concretion from ethyl ether, 36 mg of [5-(2-methoxyethoxy)imidazo[1,2-a]pyridin-2-yl](phenyl)methanone in the form of a pink solid.

Example 8

N-(2-Benzoylimidazo[1,2-a]pyridin-6-yl)acetamide 8.1 (6-Nitroimidazo[1,2-a]pyridin-2-yl)(phenyl)methanone To a solution of 0.48 g of 3-bromo-1-phenylpropane-1,2-dione in a mixture of 3 mL of THF and 0.5 mL of ethanol is added 0.25 g of 2-amino-5-nitropyridine. The reaction mixture is heated for 15 minutes at 160° C. in a microwave machine. The solid formed is separated out, taken up in 3 mL of ethanol and refluxed for 6 hours. After evaporating off the solvent, the residue is taken up in ethyl acetate and diluted with sodium hydroxide solution. The organic phase is washed with water, dried and then evaporated to give 0.42 g of (6-nitroimidazo[1,2-a]pyridin-2-yl)(phenyl)methanone in the form of a brown solid, which is used without further purification.

$^1$H NMR spectrum (DMSO-d6, δ in ppm): 7.60 (broad t, J=7.5 Hz, 2H); 7.71 (broad t, J=7.5 Hz, 1H); 7.88 (broad d, J=10.0 Hz, 1H); 8.06 (dd, J=2.5 and 10.0 Hz, 1H); 8.30 (broad d, J=8.0 Hz, 2H); 8.84 (d, J=1.0 Hz, 1H); 9.94 (dd, J=1.0 and 2.5 Hz, 1H).

Mass spectrum (CI): m/z 268 (base peak), [M+H]$^+$, m/z 285: [M+NH$_4$]$^+$.

8.2 (6-Aminoimidazo[1,2-a]pyridin-2-yl)(phenyl)methanone 0.42 g of 2-benzoyl-6-nitroimidazo[1,2-a]pyridine in 20 mL of boiling ethanol is treated with 10 mL of 0.5 N sodium hydroxide solution and 2.77 g of sodium dithionite. After 10 minutes at 80° C., the reaction medium is cooled, filtered and concentrated to dryness to give the crude (6-aminoimidazo[1,2-a]pyridin-2-yl)(phenyl)methanone, which is used without further purification.

8.3
N-(2-benzoylimidazo[1,2-a]pyridin-6-yl)acetamide

The (6-aminoimidazo[1,2-a]pyridin-2-yl)(phenyl)methanone is dissolved in 7 mL of acetic acid and treated with 0.8 mL of acetic anhydride. The reaction medium is refluxed for 2 hours, cooled, filtered and concentrated to dryness. The residue is taken up in ethyl acetate and saturated sodium hydrogen carbonate solution. The organic phase is washed and concentrated, and the product obtained is chromatographed on a column of silica, eluting with a 95/5 mixture of dichloromethane and methanol. The fractions containing the expected product are combined and concentrated to give 150 mg of N-(2-benzoylimidazo[1,2-a]pyridin-6-yl)acetamide as a mixture with N-(3-benzoylimidazo[1,2-a]pyridin-6-yl)acetamide. The two isomers are separated by preparative LC/MS preparative to give 54 mg of purified N-(2-benzoylimidazo[1,2-a]pyridin-6-yl)acetamide in the form of a beige-colored solid.

Example 9

(6-Isopropenylimidazo[1,2-a]pyridin-2-yl)(phenyl) methanone 300 mg of [6-(1-hydroxy-1-methylethyl)imidazo[1,2-a]pyridin-2-yl](phenyl)methanone hydrobromide (1:1) are taken up in a mixture of 100 mL of dichloromethane and 30 mL of saturated sodium bicarbonate solution. The organic phase is separated out by settling, dried and concentrated to dryness to give 190 mg of [6-(1-hydroxy-1-methylethyl)imidazo[1,2-a]pyridin-2-yl] (phenyl)methanone, which is dissolved in 5 mL of xylene and refluxed for 2 hours, after addition of 6.5 mg of para-toluenesulfonic acid. After 16 hours at 20° C. and evaporation of the solvent, the residue is chromatographed on a cartridge of 6 g of silica, eluting with a 95/5 mixture of dichloromethane and methanol. The fractions containing the expected product are evaporated to dryness and the residue is triturated in ethyl ether to give 60 mg of (6-isopropenylimidazo[1,2-a]pyridin-2-yl)(phenyl) methanone in the form of a pale yellow solid.

Example 10

2-Benzoyl-N,N-dimethylimidazo[1,2-a]pyridine-6-carboxamide 10.1 2-Benzoylimidazo[1,2-a]pyridine-6-acid hydrobromide (1:1)

To a suspension of 0.33 g of 6-aminonicotinic acid in 5 mL of THF and 3 mL of ethanol is added a solution of 0.654 g of 3-bromo-1-phenylpropane-1,2-dione in 2 mL of THF. The reaction mixture is stirred at 45° C. for 16 hours and for 24 hours at 20° C., and then evaporated to dryness. The residue is taken up in dichloromethane and the solid is filtered off and washed with dichloromethane to give 0.78 g of 2-benzoylimidazo[1,2-a]pyridine-6-carboxylic acid hydrobromide in the form of a yellow solid.

10.2 2-Benzoyl-N,N-dimethylimidazo[1,2-a]pyridine-6-carboxamide

A solution of 0.21 g of 2-benzoylimidazo[1,2-a]pyridine-6-carboxylic acid hydrobromide, 0.35 g of EDCI hydrochloride and 0.294 g of HOBT in 7 mL of DMF is stirred for 30 minutes at 20° C., followed by addition of 1 mL of a 1 M solution of dimethylamine in THF, and the mixture is stirred for 2 hours at 20° C. The reaction mixture is concentrated to dryness and then taken up in 100 mL of water and 200 mL of ethyl acetate. The organic phase is separated out, dried and evaporated. The residue is purified by flash chromatography on a column of 20 g of silica, eluting with a 99/1 mixture of dichloromethane and methanol. The fractions containing the expected product are combined and concentrated under vacuum to give 40 mg of 2-benzoyl-N,N-dimethylimidazo[1,2-a]pyridine-6-carboxamide in the form of a beige-colored solid.

Example 11

2-Benzoyl-N-methylimidazo[1,2-a]pyridine-6-carboxamide

By working as in Example 10, replacing the dimethylamine with methylamine, 29 mg of 2-benzoyl-N-methylimidazo[1,2-a]pyridine-6-carboxamide are obtained in the form of an off-white powder.

Example 12

Phenyl(6-vinylimidazo[1,2-a]pyridin-2-yl)methanone

A mixture of 0.4 g of (6-iodolimidazo[1,2-a]pyridin-2-yl)(phenyl)methanone, 120 mg of tetrakis(triphenylphosphine) palladium(0), 336 µL of tributylvinyltin and 20 mL of DMF is heated for 5 minutes at 130° C. in a microwave machine and then for a further 5 minutes at 130° C. after addition of 70 mg of tetrakis(triphenylphosphine)-palladium(0) and 200 µL of tributylvinyltin. The reaction mixture is concentrated to dryness, taken up in 50 mL of water and extracted with twice 50 mL of ethyl acetate. The combined organic phases are washed with saturated sodium chloride solution, dried over magnesium sulfate and evaporated to dryness under reduced pressure. The residue is chromatographed on a cartridge of silica, eluting with a mixture of cyclohexane and ethyl acetate (gradient from 10 to 30%). The fractions containing the expected product are combined and concentrated to dryness under reduced pressure to give 0.13 g of phenyl(6-vinylimidazo[1,2-a]pyridin-2-yl)methanone in the form of a yellow solid.

Example 13

(6-Ethylimidazo[1,2-a]pyridin-2-yl)(phenyl)methanone

A solution of 80 mg of phenyl(6-vinylimidazo[1,2-a]pyridin-2-yl)methanone in 20 mL of methanol is hydrogenated for 45 minutes at 45° C. under 1 bar of hydrogen in the presence of 34 mg of 10% palladium-on-charcoal. The product is chromatographed on silica, eluting with a gradient of cyclohexane and ethyl acetate, to give 15 mg of (6-ethylimidazo[1,2-a]pyridin-2-yl)(phenyl)methanone in the form of a white solid.

The intermediates described hereinbelow are useful for preparing the compounds of the present invention.

2-(6-Aminopyridin-3-yl)propan-2-ol

To a solution of 0.7 g of methyl 6-aminonicotinate in 65 mL of THF, cooled to 10° C. and under argon, are added dropwise 15 mL of a 3M solution of methylmagnesium chloride in THF. The reaction mixture is stirred for 15 hours, while allowing the temperature to rise to 20° C., and is then cooled again in an ice bath. 100 mL of saturated ammonium chloride solution and then 200 mL of ethyl acetate are added slowly. The organic phase is dried and concentrated to dryness. The residue is taken up in ethyl acetate. The precipitate is filtered off by suction and dried to give 0.4 g of 2-(6-aminopyridin-3-yl)propan-2-ol in the form of a pale yellow solid.

$^1$H NMR spectrum (DMSO-d6, δ in ppm): 1.36 (s, 6H); 4.82 (s, 1H); 5.67 (broad s, 2H); 6.37 (d, J=9.0 Hz, 1H); 7.42 (dd, J=2.5 and 9.0 Hz, 1H); 7.98 (d, J=2.5 Hz, 1H)

Mass spectrum (EI): m/z 152: [M+.], m/z 137: [M+.]-CH3 (base peak)

1-[6-(2,5-Dimethylpyrrol-1-yl)-pyridin-3-yl]propan-1-ol

To a solution of 2 g of 5-bromo-2-(2,5-dimethylpyrrol-1-yl)pyridine in 30 mL of tert-butyl methyl ether cooled to −78° C. are added slowly, under argon, 3.3 mL of a 2.5M solution of butyllithium in hexane, the mixture is then stirred for 40 minutes at about −70° C., followed by addition of a solution of 0.5 g of propionaldehyde in 5 mL of tert-butyl methyl ether. The mixture is stirred for 30 minutes at about −70° C., 20 mL of water are then added slowly and the resulting mixture is allowed to warm to 20° C. The aqueous phase is extracted with twice 100 mL of ethyl acetate and the organic phases are combined, dried and concentrated to dryness. The residue is purified by flash chromatography on a cartridge of 70 g of silica, eluting with dichloromethane and then with an 80/20 mixture of dichloromethane and ethyl acetate. The fractions containing the expected product are combined and concentrated under vacuum to give 1.07 g of 1-[6-(2,5-dimethylpyrrol-1-yl)pyridin-3-yl]propan-1-ol in the form of a yellow oil.

$^1$H NMR spectrum (DMSO-d6, δ in ppm): 0.87 (t, J=7.5 Hz, 3H); 1.69 (m, 2H); 2.02 (s, 6H); 4.60 (m, 1H); 5.37 (d, J=4.5 Hz, 1H); 5.78 (s, 2H); 7.34 (d, J=8.0 Hz, 1H); 7.89 (dd, J=2.5 and 8.0 Hz, 1H); 8.51 (d, J=2.5 Hz, 1H).

Mass spectrum (EI): m/z=230 [M]+ (base peak) m/z=215 [M-CH3]+.

2-Amino-5-(1-ethoxypropyl)pyridine

To a solution of 1.07 g of 1-[6-(2,5-dimethylpyrrol-1-yl)pyridin-3-yl]propan-1-ol in 20 mL of ethanol heated to 80° C. is added a solution of 1.94 g of hydroxylamine hydrochloride in 1.6 mL of water, and the mixture is stirred for 24 hours at 80° C. After cooling to room temperature, the reaction medium is filtered and concentrated to dryness. The residue is purified by flash chromatography on a column of 100 g of silica, eluting with 400 mL of dichloromethane, then with 300 mL of ethyl acetate and then with a 95/5 mixture of dichloromethane and methanol. The fractions containing the expected product are combined and concentrated under vacuum to give 0.186 g of 2-amino-5-(1-ethoxypropyl)pyridine in the form of a brown oil.

$^1$H NMR spectrum (DMSO-d6, δ in ppm): 0.78 (t, J=7.5 Hz, 3H); 1.06 (t, J=7.0 Hz, 3H); 1.53 (m, 1H); 1.70 (m, 1H); 3.24 (partially masked q, J=7.0 Hz, 2H); 4.02 (t, J=7.0 Hz, 1H); 6.48 (broad m, 2H); 6.61 (d, J=9.0 Hz, 1H); 7.47 (dd, J=2.5 and 9.0 Hz, 1H); 7.79 (d, J=2.5 Hz, 1H).

Mass spectrum (EI): m/z=180 [M]+, m/z=151 [M-C2H5]+, m/z=123 [m/z=151-C2H4]+, m/z=77 [C6H5]+ (base peak).

6-Aminopyridine-3-carboxaldehyde

To a suspension of 1 g of 6-aminopyridine-3-carbonitrile in 20 mL of toluene cooled to −78° C. are added dropwise 15 mL of a 1.2 M solution of diisobutylaluminum hydride in toluene. The reaction medium is stirred for 30 minutes at −78° C. and is then allowed to warm slowly to 20° C. After cooling again to −78° C., 6 mL of water are added slowly and the resulting mixture is stirred for 1 hour at −78° C. The reaction medium is stirred for 16 hours at 20° C., treated with 20 mL of 2.5 N hydrochloric acid, stirred for 20 minutes, basified by addition of concentrated sodium hydroxide and extracted three times with 100 mL of dichloromethane. The combined organic phases are dried and concentrated to dryness under reduced pressure. The residue is taken up in 40 mL of ethyl acetate and 40 mL of saturated sodium bisulfite solution. The aqueous phase is washed twice with 40 mL of ethyl acetate, basified to about pH 14 by addition of concentrated sodium hydroxide, and extracted three times with 50 mL of dichloromethane. The combined organic phases are dried and concentrated to dryness under reduced pressure to give 200 mg of crude 6-aminopyridine-3-carboxaldehyde in the form of a yellow powder, which is used without further purification.

6-Bromo-5-methylimidazo[1,2-a]pyridine-2-carboxylic acid

To a solution of 0.283 g of ethyl 6-bromo-5-methylimidazo[1,2-a]pyridine-2-carboxylate in 2 mL of ethanol is added 1 mL of 1 N sodium hydroxide. The reaction mixture is refluxed for 3 hours. After cooling, the reaction medium is acidified with acetic acid. The solid formed is filtered off, washed with water and then dried under vacuum to give 0.195 g of 6-bromo-5-methylimidazo[1,2-a]pyridine-2-carboxylic acid in the form of a white solid.

$^1$H NMR spectrum (DMSO-d6, δ in ppm): 2.77 (s, 3H); from 7.46 to 7.53 (m, 2H); 8.42 (s, 1H).

Mass spectrum (EI): m/z 254 (base peak): [M+.], m/z 210: [M+.]-CO$_2$H, m/z 170: 210-C2HN

N-Methoxy-N-methyl-6-chloroimidazo[1,2-a]pyridine-2-carboxamide

To a solution of 0.784 g of 6-chloroimidazo[1,2-a]pyridine-2-carboxylic acid in 12 mL of dichloromethane are added 1.67 mL of triethylamine, 1.53 g of 1-(3-dimethylaminopropyl)-3-ethylcarbodiimide hydrochloride and 1.08 g of 1-hydroxybenzotriazole. The reaction mixture is stirred for 20 minutes at room temperature. 0.39 g of N,O-dimethylhydroxylamine hydrochloride is added. The reaction mixture is stirred for 4 hours at room temperature. 60 mL of dichloromethane and 30 mL of water are added. After separation of the phases by settling, the organic phase is dried over magnesium sulfate, filtered, evaporated to dryness under reduced pressure, and then purified on a column of silica, eluting with a 95/5 mixture by volume of dichloromethane and methanol. The fractions containing the product are combined and concentrated to dryness under reduced pressure to give 0.6 g of N-methoxy-N-methyl-6-chloroimidazo[1,2-a]pyridine-2-carboxamide in the form of a white solid.

$^1$H NMR spectrum (DMSO-d6, δ in ppm): 3.42 (broad s, 3H); 3.75 (s, 3H); 7.37 (dd, J=2.0 and 9.5 Hz, 1H); 7.67 (d, J=9.5 Hz, 1H); 8.39 (s, 1H); 8.85 (d, J=2.0 Hz, 1H).

Mass spectrum (LCMS): m/z 240: [M+H]$^+$.

N-Methoxy-N-methyl-5-methylimidazo[1,2-a]pyridine-2-carboxamide

N-Methoxy-N-methyl-5-methylimidazo[1,2-a]pyridine-2-carboxamide is prepared according to the procedure described above, starting with 5-methylimidazo[1,2-a]pyridine-2-carboxylic acid.

$^1$H NMR spectrum (DMSO-d6, δ in ppm): 2.64 (s, 3H); 3.47 (broad s, 3H); 3.77 (s, 3H); 6.85 (broad d, J=7.0 Hz, 1H); 7.30 (dd, J=7.0 and 9.0 Hz, 1H); 7.51 (broad d, J=9.0 Hz, 1H); 8.21 (s, 1H).

Mass spectrum (EI): m/z 219: [M+.], m/z 188: [M+.]-OCH3, m/z 159 (base peak): [M+.]-C2H6NO.

N-Methoxy-N-methyl-6-bromo-5-methylimidazo[1,2-a]pyridine-2-carboxamide

N-Methoxy-N-methyl-6-bromo-5-methylimidazo[1,2-a]pyridine-2-carboxamide is prepared according to the procedure described above, starting with 6-bromo-5-methylimidazo[1,2-a]pyridine-2-carboxylic acid.

$^1$H NMR spectrum (DMSO-d6, δ in ppm): 2.77 (s, 3H); 3.45 (broad s, 3H); 3.77 (s, 3H); from 7.48 to 7.53 (m, 2H); 8.33 (s, 1H).

Mass spectrum (EI): m/z 297: [M$^+$], m/z 266: [M$^+$]-OMe, m/z 237 (base peak): [M$^+$]-C2H6NO.

N,N-Dimethyl-6-nitropyridine-3-amine

To a solution of 1 g of 5-bromo-2-nitropyridine in 5 mL of ethanol are added 6 mL of a 2 M solution of dimethylamine in tetrahydrofuran. The reaction mixture is heated for 2 hours at 140° C. in a microwave machine. After cooling, the solid formed is separated off and washed with ethyl ether to give 850 mg of N,N-dimethyl-6-nitropyridine-3-amine in the form of a yellow solid.

$^1$H NMR spectrum (DMSO-d6, δ in ppm): 3.12 (s, 6H); 7.21 (dd, J=3.0 and 9.5 Hz, 1H); 8.02 (d, J=3.0 Hz, 1H); 8.15 (d, J=9.5 Hz, 1H)

Mass spectrum (EI): m/z 167 (base peak): [M$^+$], m/z 137: [M$^+$]-NO, m/z 121: [M$^+$]-NO$_2$.

5-Dimethylaminopyridine-2-amine

The N,N-dimethyl-6-nitropyridine-3-amine obtained above is taken up in 25 mL of ethanol. After addition of 4.8 g of stannous chloride, the reaction mixture is refluxed for 30 minutes and then concentrated to dryness. The residue is chromatographed on a column of silica, eluting with a 90/10 mixture of dichloromethane and ammoniacal methanol. The fractions containing the expected product are combined and concentrated to give 750 mg of 5-dimethylaminopyridine-2-amine in the form of a pasty yellow solid.

$^1$H NMR spectrum (DMSO-d6, δ in ppm): 2.80 (s, 6H); 6.94 (d, J=9.5 Hz, 1H); 7.18 (d, J=3.0 Hz, 1H); 7.32 (broad s, 2H); 7.83 (dd, J=3.0 and 9.5 Hz, 1H)

Mass spectrum (EI): m/z 137 (base peak): [M+.], m/z 122: [M+.]-CH3.

Ethyl 6-dimethylaminoimidazo[1,2-a]pyridine-2-carboxylate

To a suspension of 0.2 g of 5-dimethylaminopyridine-2-amine in 3 mL of DME are added 215 μL of ethyl bromopyruvate. The reaction mixture is stirred at 20° C. for 16 hours and then, after addition of 3 mL of ethanol, for 16 hours at reflux, and finally concentrated under reduced pressure. The residue is filtered on a cartridge of 15 g of silica, eluting with a mixture of dichloromethane and methanol (98/2). The fractions containing the expected product are combined and washed with saturated sodium bicarbonate solution. The organic phase is dried and concentrated to dryness under reduced pressure to give 76 mg of ethyl 6-dimethylaminoimidazo[1,2-a]pyridine-2-carboxylate in the form of a green oil, which is used without further purification in the rest of the synthesis.

The tables that follow illustrate the chemical structures (Table 1) and the spectroscopic characteristics (Table 2) of a number of examples of compounds according to the invention.

TABLE 1

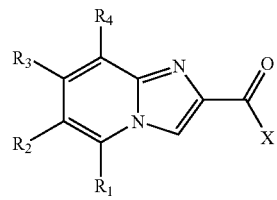

(I)

| Compound | $R_1$ | $R_2$ | $R_3$ | $R_4$ | X | Salt |
|---|---|---|---|---|---|---|
| 1 | H | Me | H | H | Ph | HCl |
| 2 | H | ~CF$_3$ | H | H | Ph | HCl |
| 3 | H | ~CMe$_2$OH | H | H | Ph | HBr |
| 4 | H | ~CH$_2$OH | H | H | Ph | |
| 5 | H | Cl | H | H |  | |
| 6 | H | Ph | H | H | Ph | |
| 7 | 2-methoxy-ethoxy | H | H | H | Ph | |
| 8 | H | ~NHCOMe | H | H | Ph | |
| 9 | H | ~CMe=CH$_2$ | H | H | Ph | |
| 10 | H | ~CONMe$_2$ | H | H | Ph | |
| 11 | H | ~CONHMe | H | H | Ph | |
| 12 | H | ~CH=CH$_2$ | H | H | Ph | |
| 13 | H | ~CH$_2$CH$_3$ | H | H | Ph | |
| 14 | H | F | H | H | Ph | |
| 15 | H | Cl | H | Cl | Ph | HCl |

TABLE 1-continued
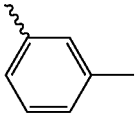
(I)
| Compound | R₁ | R₂ | R₃ | R₄ | X | Salt |
|---|---|---|---|---|---|---|
| 16 | H | H | Cl | H | Ph | |
| 17 | H | Br | H | H | Ph | |
| 18 | Br | H | H | H | Ph | |
| 19 | H | ~CN | H | H | Ph | |
| 20 | NH₂ | H | H | H | Ph | |
| 21 | H | ~CONH₂ | H | H | Ph | |
| 22 | H | I | H | H | Ph | HBr |
| 23 | H | H | OH | H | Ph | HBr |
| 24 | H | F | H | F | Ph | HBr |
| 25 | H | ~CO₂Me | H | H | Ph | HBr |
| 26 | H | 1-ethoxypropyl | H | H | Ph | |
| 27 | H | ~COMe | H | H | Ph | |
| 28 | H | ~CH=O | H | H | Ph | |
| 29 | H | Cl | H | H | 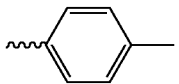 | |
| 30 | H | Cl | H | H | 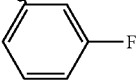 | |
| 31 | H | Cl | H | H |  | |
| 32 | H | Cl | H | H | 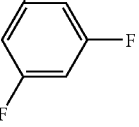 | |
| 33 | H | Cl | H | H | 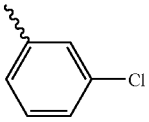 | |
| 34 | Me | H | H | H | Ph | |
| 35 | Me | Br | H | H | Ph | |
| 36 | H | Cl | H | H | 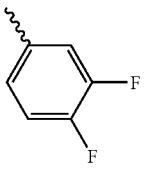 | |
| 37 | H | Cl | H | H |  | |
| 38 | H | ~N(CH₃)₂ | H | H | Ph | PF₆ |

TABLE 1-continued (I)

| Compound | R₁ | R₂ | R₃ | R₄ | X | Salt |
|---|---|---|---|---|---|---|
| 39 | H | 3-(hydroxymethyl)phenyl | H | H | Ph | |
| 40 | H | 4-(hydroxymethyl)phenyl | H | H | Ph | |
| 41 | H | 2-(hydroxymethyl)phenyl | H | H | Ph | |
| 42 | H | 3-formylphenyl | H | H | Ph | |
| 43 | Me | Me | H | H | Ph | |

TABLE 2

| Compound | Characterizations |
|---|---|
| 1 | ¹H NMR spectrum (DMSO-d6, δ in ppm): 2.40 (s, 3H); 7.65 (m, 3H); 7.77 (broad t, J = 7.5 Hz, 2H); 8.18 (broad d, J = 8.0 Hz, 2H); 8.57 (broad s, 1H); 8.79 (s, 1H). Mass spectrum (EI): m/z 236: [M⁺·] (base peak), m/z 208: [M − CO]⁺. IR spectrum (KBr): 3047; 2796; 1650; 1565; 1259; 1229; 917; 806; 727 and 702 cm⁻¹ |
| 2 | ¹H NMR spectrum (DMSO-d6, δ in ppm): from 7.55 to 7.76 (m, 4H); 7.94 (d, J = 8.5 Hz, 1H); 8.30 (broad d, J = 8.0 Hz, 2H); 8.74 (s, 1H); 9.32 (broad s, 1H). Mass spectrum (EI): m/z 290: [M⁺·] (base peak), m/z 261: [M − CO]⁺. IR spectrum (KBr): 3062; 2748; 1665; 1577; 1385; 1340; 1297; 1223; 1170; 1140; 1066; 916; 723 and 673 cm⁻¹. |
| 3 | ¹H NMR spectrum (DMSO-d6, δ in ppm): 1.50 (s, 6H); 7.60 (broad t, J = 7.5 Hz, 2H); from 7.67 to 7.74 (m, 3H); 8.23 (broad d, J = 8.0 Hz, 2H); 8.71 (broad s, 1H); 8.77 (broad s, 1H). Mass spectrum (EI): m/z 280 (base peak): [M]⁺, m/z 265: [M − CH₃]⁺, m/z 105: [PhCO]⁺ IR spectrum (KBr): 2975; 1657; 1596; 1558; 1286; 1180; 914 and 723 cm⁻¹. |
| 4 | ¹H NMR spectrum (DMSO-d6, δ in ppm): 4.54 (dd, J = 1.5 and 6.0 Hz, 2H); 5.44 (t, J = 6.0 Hz, 1H); 7.32 (dd, J = 1.5 and 9.5 Hz, 1H); 7.57 (broad t, J = 7.5 Hz, 2H); from 7.64 to 7.70 (m, 3H); 8.32 (broad d, J = 8.0 Hz, 2H); 8.53 (broad m, 1H); 8.65 (d, J = 1.0 Hz, 1H). IR spectrum (KBr): 3393; 1624; 1599; 1546; 1275; 1257; 1240; 1061; 899; 802; 725 and 694 cm⁻¹. Mass spectrum (EI): m/z = 252 [M]⁺ (base peak), m/z = 223 [M − CHO]⁺, m/z = 105 [PhCO]⁺, m/z = 77 [C₆H₅]⁺. |
| 5 | ¹H NMR spectrum (DMSO-d6, δ in ppm): 2.31 (s, 3H); from 7.29 to 7.39 (m, 2H); from 7.41 to 7.50 (m, 2H); 7.60 (broad d, J = 8.0 Hz, 1H); 7.71 (d, J = 10.0 Hz, 1H); 8.44 (s, 1H); 8.85 (d, J = 2.5 Hz, 1H). Mass spectrum (EI): m/z 270: [M⁺·], m/z 241 (base peak): [M − CO]⁺. |
| 6 | ¹H NMR spectrum (DMSO-d6, δ in ppm): 7.44 (broad t, J = 7.5 Hz, 1H); 7.54 (broad t, J = 7.5 Hz, 2H); 7.59 (broad t, J = 7.5 Hz, 2H); 7.69 (broad t, J = 7.5 Hz, 1H); from 7.72 to 7.79 (m, 3H); 7.82 (d, J = 9.5 Hz, 1H); 8.34 (broad d, J = 8.0 Hz, 2H); 8.64 (s, 1H); 9.00 (broad s, 1H). IR spectrum (KBr): 1643; 1542; 1503; 1264; 893; 758; 716; 698 and 684 cm⁻¹. Mass spectrum (ES): m/z = 299 [MH]⁺ (base peak). |
| 7 | ¹H NMR spectrum (DMSO-d6, δ in ppm): 3.37 (s, 3H); 3.82 (m, 2H); 4.50 (m, 2H); 6.53 (d, J = 7.5 Hz, 1H); 7.35 (d, J = 7.5 Hz, 1H); 7.44 (t, J = 7.5 Hz, 1H); 7.58 (t, J = 7.5 Hz, 2H); 7.68 (t, J = 7.5 Hz, 1H); 8.29 (s, 1H); 8.31 (d, J = 8.0 Hz, 2H) (broad absorptions): Mass spectrum (EI): m/z 296 (base peak): [M⁺·], m/z 238: [M⁺·] − CH₃O(CH₂)₂, m/z 59: CH₃O(CH₂)₂⁺. IR spectrum (KBr): 3182; 1643; 1543; 1344; 1271; 1237; 1126; 1024; 914; 853; 772; 731; 704 and 679 cm⁻ |
| 8 | ¹H NMR spectrum (DMSO-d6, δ in ppm): 2.11 (s, 3H); 7.28 (dd, J = 2.0 and 9.5 Hz, 1H); 7.56 (broad t, J = 7.5 Hz, 2H); 7.66 (m, 2H); 8.30 (broad d, J = 8.0 Hz, 2H); 8.73 (s 1H); 9.32 (broad s, 1H); 10.2 (broad s, 1H). Mass spectrum (EI): m/z 279: [M⁺·], m/z 237: [M⁺·] − COCH3, m/z 43 (base peak): COCH₃⁺. IR spectrum (KBr): 3267; 1668; 1638; 1539; 1369; 1280; 1243; 1012; 894; 813 and 718 cm⁻¹. |
| 9 | ¹H NMR spectrum (DMSO-d6, δ in ppm): 2.15 (s, 3H); 5.25 (broad s, 1H); 5.63 (s, 1H); 7.58 (broad t, J = 7.5 Hz, 2H); from 7.64 to 7.73 (m, 3H); 8.32 (broad d, J = 8.0 Hz, 2H); |

TABLE 2-continued

| Compound | Characterizations |
|---|---|
| | 8.60 (s, 1H); 8.73 (broad s, 1H).<br>IR spectrum (KBr): 1636; 1577; 1539; 1268; 1230; 897; 808 and 708 cm$^{-1}$<br>Mass spectrum (EI) m/z = 262 [M]$^+$,<br>m/z = 233 [M − C$_2$H$_5$]$^+$, m/z = 105 [C$_7$H$_5$O]$^+$,<br>m/z = 77 [C$_6$H$_5$]$^+$ (base peak). |
| 10 | $^1$H NMR spectrum (DMSO-d6, δ in ppm): 3.03 (s, 6H); 7.42 (d, J = 7.5 Hz, 1H); from 7.51 to 7.79 (m, 4H); 8.30 (d, J = 8.0 Hz, 2H); 8.64 (s, 1H); 8.83 (s, 1H).<br>IR spectrum (KBr): 1647; 1617; 1496; 1398; 1281; 1241; 895 and 725 cm$^{-1}$.<br>Mass spectrum (ES): m/z = 294 [MH]$^+$ (base peak). |
| 11 | $^1$H NMR spectrum (DMSO-d6, δ in ppm) 2.81 (d, J = 4.5 Hz, 3H); from 7.52 to 7.73 (m, 3H); 7.78 (m, 2H); 8.31 (d, J = 8.0 Hz, 2H); 8.64 (m, 1H); 8.74 (s, 1H); 9.16 (s, 1H).<br>IR spectrum (KBr): 1650; 1626; 1599; 1576; 1554; 1532; 1271; 1235 and 719 cm$^{-1}$.<br>Mass spectrum (EI): m/z = 279 [M]$^+$ (base peak), m/z = 249 [M − CH$_4$N]$^+$,<br>m/z = 105 [C$_7$H$_5$O]$^+$, m/z = 77 [C$_6$H$_5$]$^+$. |
| 12 | $^1$H NMR spectrum (DMSO-d6, δ in ppm): 5.40 (d, J = 11.0 Hz, 1H); 5.93 (d, J = 17.5 Hz, 1H); 6.77 (dd, J = 11.0 and 17.5 Hz, 1H); 7.58 (broad t, J = 7.5 Hz, 2H); 7.67 (broad t partially masked, J = 7.5 Hz, 1H); 7.69 (broad s, 2H); 8.31 (broad d, J = 8.0 Hz, 2H); 8.59 (s, 1H); 8.64 (broad s, 1H).<br>Mass spectrum (ES): m/z 249 [M + H$^+$]. |
| 13 | $^1$H NMR spectrum (DMSO-d6, δ in ppm): 1.23 (t, J = 7.5 Hz, 3H); 2.64 (q, J = 7.5 Hz, 2H); 7.31 (dd, J = 2.0 and 9.5 Hz, 1H); 7.57 (t, J = 7.5 Hz, 2H); from 7.62 to 7.70 (m, 2H); 8.31 (broad d, J = 7.5 Hz, 2H); 8.43 (broad s, 1H); 8.55 (s, 1H). |
| 14 | $^1$H NMR spectrum (DMSO-d6, δ in ppm): 7.50 (ddd, J = 2.5-8.5 and 11.0 Hz, 1H); 7.59 (broad t, J = 7.5 Hz, 2H); 7.69 (broad t, J = 7.5 Hz, 1H); 7.81 (dd, J = 5.0 and 8.5 Hz, 1H); 8.31 (broad d, J = 8.0 Hz, 2H); 8.61 (s, 1H); 8.82 (dd, J = 2.5 and 5.0 Hz, 1H).<br>Mass spectrum (EI): m/z 240: [M$^{+\cdot}$] (base peak).<br>IR spectrum: 3146; 3059; 1644; 1539; 1257; 1233; 1172; 1012; 894; 719 and 690 cm$^{-1}$ |
| 15 | $^1$H NMR spectrum (DMSO-d6, δ in ppm): 7.60 (broad t, J = 7.5 Hz, 2H); 7.70 (broad t, J = 7.5 Hz, 1H); 7.82 (d, J = 2.0 Hz, 1H); 8.30 (broad d, J = 8.5 Hz, 2H); 8.66 (s, 1H); 8.90 (d, J = 2.0 Hz, 1H). |
| 16 | $^1$H NMR spectrum (DMSO-d6, δ in ppm): 7.13 (dd, J = 2.5 and 7.0 Hz, 1H); 7.57 (broad t, J = 7.5 Hz, 2H); 7.68 (broad t, J = 7.5 Hz, 1H); 7.92 (d, J = 2.5 Hz, 1H); 8.28 (broad d, J = 8.0 Hz, 2H); 8.65 (m, 2H)<br>Mass spectrum (EI): m/z 256 (base peak): [M$^+$], m/z 228: [M$^{+\cdot}$] − [CO], m/z 77: Ph$^+$ |
| 17 | $^1$H NMR spectrum (DMSO-d6, δ in ppm): 7.51 (dd, J = 2.0 and 9.5 Hz, 1H); 7.58 (broad t, J = 7.5 Hz, 2H); 7.68 (broad t, J = 7.5 Hz, 1H); 7.71 (d, J = 9.5 Hz, 1H); 8.30 (broad d, J = 8.0 Hz, 2H); 8.57 (s, 1H); 8.98 (broad s, 1H).<br>Mass spectrum (EI): m/z 300 (base peak): [M$^+$], m/z 272: [M − CO]$^+$, m/z 105: PhCO$^+$.<br>IR spectrum (CCl$_4$): 3152; 1651; 1528; 1261; 1233; 1055; 1010; 893; 713 and 686 cm$^{-1}$. |
| 18 | $^1$H NMR spectrum (DMSO-d6, δ in ppm): 7.39 (dd, J = 7.5 and 9.0 Hz, 1H); 7.47 (broad d, J = 7.5 Hz, 1H); 7.59 (broad t, J = 7.5 Hz, 2H); 7.70 (broad t, J = 7.5 Hz, 1H); 7.82 (broad d, J = 9.0 Hz, 1H); 8.33 (broad d, J = 8.0 Hz, 2H); 8.48 (s, 1H)<br>Mass spectrum (LCMS): m/z 300 (base peak): [M + H]$^+$.<br>IR spectrum (KBr): 3156; 1639; 1511; 1260; 1237; 1179; 1125; 895; 775; 705 and 697 cm$^{-1}$. |
| 19 | $^1$H NMR spectrum (DMSO-d6, δ in ppm): from 7.55 to 7.74 (m, 4H); 7.89 (d, J = 9.5 Hz, 1H); 8.29 (broad d, J = 8.0 Hz, 2H); 8.68 (s, 1H); 9.40 (broad s, 1H)<br>Mass spectrum (EI): m/z 247 (base peak): [M$^{+\cdot}$], m/z 218: [M − CO]$^+$, m/z 192: 219 − [CO].<br>IR spectrum (KBr): 3144; 2230; 1649; 1321; 1225; 1158; 1008; 906 and 729 cm$^{-1}$. |
| 20 | $^1$H NMR spectrum (DMSO-d6, δ in ppm): 6.04 (d, J = 7.5 Hz, 1H); 6.85 (broad s, 2H); 6.93 (d, J = 9.0 Hz, 1H); 8.25 (dd, J = 7.5 and 9.0 Hz, 1H); 7.57 (broad t, J = 7.5 Hz, 2H); 7.67 (broad t, J = 7.5 Hz, 1H); 8.33 (broad d, J = 8.0 Hz, 2H); 8.61 (s, 1H).<br>Mass spectrum (EI): m/z 237 (base peak): [M$^{+\cdot}$], m/z 207: [M − CO]$^+$.<br>IR spectrum (KBr): 3372; 3202; 3129; 1637; 1548; 1497; 1232; 910; 733 and 697 cm$^{-1}$. |
| 21 | $^1$H NMR spectrum (DMSO-d6, δ in ppm): from 7.52 to 7.85 (m, 6H); 8.14 (broad s, 1H); 8.31 (broad d, J = 8.0 Hz, 2H); 8.73 (s, 1H); 9.20 (broad s, 1H)<br>Mass spectrum (EI): m/z 265 (base peak): [M$^+$], m/z 237: [M − CO]$^+$, m/z 77: Ph$^+$.<br>IR spectrum (KBr): 3428; 3190; 3144; 1682; 1626; 1483; 1394; 1275; 1241; 1011; 893; 733 and 521 cm$^{-1}$. |
| 22 | $^1$H NMR spectrum (DMSO-d6, δ in ppm): from 7.57 to 7.66 (m, 3H); 7.73 (t, J = 7.5 Hz, 1H); 7.80 (d, J = 9.5 Hz, 1H); 8.21 (d, J = 8.0 Hz, 2H); 8.66 (s, 1H); 9.09 (s, 1H) (broad absorptions)<br>Mass spectrum (EI): m/z 348 (base peak): [M$^+$], m/z 320: [M − CO]$^+$, m/z 271: [M$^+$] − Ph.<br>IR spectrum (KBr): 3054; 1660; 1648; 1593; 1357; 1268; 1226; 1012; 911; 723 and 598 cm$^{-1}$. |
| 23 | $^1$H NMR spectrum (DMSO-d6, δ in ppm): 6.67 (dd, J = 2.5 and 7.5 Hz, 1H); 6.75 (d, J = 2.5 Hz, 1H); 7.55 (broad t, J = 7.5 Hz, 2H); 7.65 (broad t, J = 7.5 Hz, 1H); 8.26 (broad d, J = 8.0 Hz, 2H); 8.40 (s, 1H); 8.43 (d, J = 7.5 Hz, 1H); 10.5 (s, 1H)<br>Mass spectrum (EI): m/z 238 (base peak): [M$^+$], m/z 210: [M − CO]$^+$, m/z 105: PhCO$^+$.<br>IR spectrum (KBr): 3165; 2597; 1637; 1551; 1234; 1160; 907; 714 and 698 cm$^{-1}$. |
| 24 | $^1$H NMR spectrum (DMSO-d6, δ in ppm): 7.59 (broad t, J = 7.5 Hz, 2H); 7.70 (m, 2H); 8.29 (broad d, J = 8.0 Hz, 2H); 8.74 (d, J = 3.0 Hz, 1H); 8.77 (m, 1H).<br>Mass spectrum (EI): m/z 258 (base peak): [M$^+$], m/z 230: [M − CO]$^+$, m/z 239: [M$^+$] − F.<br>IR spectrum (KBr): 3066; 3036; 2667; 1650; 1601; 1573; 1451; 1348; 1285; 1247; 1149; 914; 858 and 719 cm$^{-1}$. |
| 25 | $^1$H NMR spectrum (DMSO-d6, δ in ppm): 3.92 (s, 3H); 7.60 (broad t, J = 7.5 Hz, 2H); 7.71 (broad t, J = 7.5 Hz, 1H); 7.81 (m, 2H); 8.28 (broad d, J = 8.0 Hz, 2H); 8.83 (s, 1H); 9.44 (m, 1H)<br>Mass spectrum (EI): m/z 280 (base peak): [M$^+$], m/z 265: [M$^+$] − CH3, m/z 252: [M − CO]$^+$, m/z 105: PhCO$^+$, m/z 77: Ph$^+$.<br>IR spectrum (KBr): 3063; 2750; 1730; 1654; 1577; 1435; 1322; 1215; 1103; 1010; 910; 766; 719 and 682 cm$^{-1}$. |
| 26 | $^1$H NMR spectrum (DMSO-d6, δ in ppm): 0.85 (t, J = 7.5 Hz, 3H); 1.12 (t, J = 7.0 Hz, 3H); from 1.59 to 1.85 (m, 2H); 3.37 (partially masked q, J = 7.0 Hz, 2H); 4.26 (t, J = 7.0 Hz, 1H); 7.33 (dd, J = 1.5 and 9.5 Hz, 1H); 7.57 (broad t, J = 7.5 Hz, 2H); from 7.64 to 7.74 (m, 2H); 8.32 (broad d, J = 8.0 Hz, 2H); 8.55 (broad s, 1H); 8.63 (s, 1H).<br>Mass spectrum (EI): m/z = 308 [M]$^+$,<br>m/z = 279 [M − C$_2$H$_5$]$^+$ (base peak),<br>m/z = 251 [m/z = 279 − C$_2$H$_4$]$^+$, m/z = 77 [C$_6$H$_5$]$^+$. |
| 27 | $^1$H NMR spectrum (DMSO-d6, δ in ppm): 2.62 (s, 3H); 7.59 (t, J = 7.5 Hz, 2H); 7.70 (t, J = 7.5 Hz, 1H); from 7.74 to 7.80 (m, 2H); 8.31 (d, J = 8.0 Hz, 2H); 8.72 (s, 1H); 9.51 (broad s, 1H).<br>IR spectrum (KBr): 1679; 1641; 1598; 1575; 1483; 1384; 1290; 1255; 1209; 893 and 722 cm$^{-1}$.<br>Mass spectrum (EI): m/z = 264 [M]$^+$,<br>m/z = 221 [M − COCH$_3$]$^+$, m/z = 105 [C$_7$H$_5$O]$^+$,<br>m/z = 77 [C$_6$H$_5$]$^+$ (base peak), m/z = 43 CH$_3$CO$^+$. |
| 28 | $^1$H NMR spectrum (DMSO-d6, δ in ppm): 7.59 (broad t, J = 7.5 Hz, 2H); from 7.66 to 7.74 (m, 2H); 7.82 (d, J = 9.5 Hz, 1H); 8.30 (broad d, J = 8.0 Hz, 2H); 8.83 (s, 1H); 9.38 (broad s, 1H); 10.0 (s, 1H).<br>IR spectrum (KBr): 1694; 1645; 1288; 1229; 722 and 693 cm$^{-1}$<br>Mass spectrum: (IE) m/z = 250 [M]$^+$ m/z = 221 [M − CHO]$^+$ m/z = 77 [C$_6$H$_5$]$^+$ (base peak). |

TABLE 2-continued

| Compound | Characterizations |
|---|---|
| 29 | $^1$H NMR spectrum (DMSO-d6, δ in ppm): 2.42 (s, 3H); from 7.40 to 7.52 (m, 3H); 7.78 (d, J = 9.5 Hz, 1H); 8.04 (broad s, 1H); 8.13 (broad d, J = 7.5 Hz, 1H); 8.56 (s, 1H); 8.89 (d, J = 2.5 Hz, 1H) Mass spectrum (EI): m/z 270: [M$^{+\cdot}$] base peak). |
| 30 | $^1$H NMR spectrum (DMSO-d6, δ in ppm): 2.42 (s, 3H); 7.39 (broad d, J = 8.5 Hz, 2H); 7.43 (d, J = 2.0 and 10.0 Hz, 1H); 7.79 (d, J = 10.0 Hz, 1H); 8.26 (broad d, J = 8.5 Hz, 2H); 8.56 (s, 1H); 8.90 (d, J = 2.0 Hz, 1H). Mass spectrum (EI): m/z 270 (base peak): [M$^+$], m/z 241: [M − CO]$^+$. |
| 31 | $^1$H NMR spectrum (DMSO-d6, δ in ppm): 7.45 (d, J = 2.0 and 10.0 Hz, 1H); 7.54 (m, 1H); 7.65 (m, 1H); 7.80 (d, J = 10.0 Hz, 1H); from 8.11 to 8.20 (m, 2H); 8.63 (s, 1H); 8.90 (d, J = 2.0 Hz, 1H) Mass spectrum (EI): m/z 274 (base peak): [M$^+$], m/z 246: [M − CO]$^+$. |
| 32 | $^1$H NMR spectrum (DMSO-d6, δ in ppm): 7.42 (broad t, J = 8.5 Hz, 2H); 7.45 (dd, J = 2.0 and 10.0 Hz, 1H); 7.78 (d, J = 10.0 Hz, 1H); 8.48 (broad dd, J = 5.5 and 8.5 Hz, 1H); 8.60 (s, 1H); 8.90 (d, J = 2.0 Hz, 1H); Mass spectrum (EI): m/z 274 (base peak): [M$^+$], m/z 246: [M − CO]$^+$. |
| 33 | $^1$H NMR spectrum (DMSO-d6, δ in ppm): 7.47 (dd, J = 2.0 and 10.0 Hz, 1H); 7.61 (broad t, J = 9.0 Hz, 1H); 7.81 (d, J = 10.0 Hz, 1H); 8.04 (broad d, J = 9.0 Hz, 2H); 8.66 (s, 1H); 8.90 (broad s, 1H). IR spectrum (KBr): 3148; 2924; 1643; 1591; 1534; 1441; 1314; 1213; 1124; 1078; 990; 796 and 758 cm$^{-1}$. Mass spectrum (EI): m/z 292 (base peak): [M$^{+\cdot}$], m/z 264: [M − CO]$^+$, m/z 113: COC$_6$H$_3$F$_2$. |
| 34 | $^1$H NMR spectrum (DMSO-d6, δ in ppm): 2.68 (s, 3H); 6.91 (broad d, J = 7.0 Hz, 1H); 7.36 (dd, J = 7.0 and 9.5 Hz, 1H); from 7.53 to 7.63 (m, 3H); 7.68 (broad t, J = 7.5 Hz, 1H); 8.35 (broad d, J = 8.0 Hz, 2H); 8.50 (s, 1H) Mass spectrum (EI): m/z 236: [M+·] (base peak), m/z 207: [M − CO]$^+$. IR spectrum (KBr): 2923; 1634; 1597; 1545; 1278; 1239; 1181; 897; 783; 700 and 470 cm$^{-1}$. |
| 35 | $^1$H NMR spectrum (DMSO-d6, δ in ppm): 2.82 (s, 3H); from 7.54 to 7.62 (m, 4H); 7.68 (broad t, J = 7.5 Hz, 1H); 8.32 (broad d, J = 8.0 Hz, 2H); 8.61 (s, 1H). Mass spectrum (EI): m/z 314 (base peak): [M$^{+\cdot}$], m/z 285: [M − CO]$^+$, m/z 235: [M − Br]$^+$. |
| 36 | $^1$H NMR spectrum (DMSO-d6, δ in ppm): 7.46 (dd, J = 2.0 and 9.5 Hz, 1H); 7.63 (t, J = 8.0 Hz, 1H); 7.76 (broad d, J = 8.0 Hz, 1H); 7.81 (d, J = 9.5 Hz, 1H); 8.26 (broad d, J = 8.0 Hz, 1H); 8.36 (t, J = 2.0 Hz, 1H); 8.63 (s, 1H); 8.91 (broad d, J = 2.0 Hz, 1H). Mass spectrum (CI): m/z 290, [M$^+$] |
| 37 | $^1$H NMR spectrum (DMSO-d6, δ in ppm): 7.47 (dd, J = 2.0 and 9.5 Hz, 1H); 7.67 (td, J = 8.0 and 10.5 Hz, 1H); 7.81 (d, J = 9.5 Hz, 1H); 8.31 (m, 1H); 8.46 (m, 1H); 8.64 (s, 1H); 8.91 (broad d, J = 2.0 Hz, 1H). Mass spectrum (CI): m/z 292, [M$^{+\cdot}$] |
| 38 | $^1$H NMR spectrum (DMSO-d6, δ in ppm): 2.95 (s, 6H); 7.64 (t, J = 7.5 Hz, 2H); 7.68 (d, J = 9.5 Hz, 1H); 7.76 (m, 2H); 7.99 (broad s, 1H); 8.14 (d, J = 7.5 Hz, 2H); 8.67 (s, 1H). Mass spectrum (EI): m/z 265, [M$^{+\cdot}$] (base peak). |
| 39 | $^1$H NMR spectrum (DMSO-d6, δ in ppm): 4.60 (d, J = 5.5 Hz, 2H); 5.29 (broad t, J = 5.5 Hz, 1H); 7.38 (broad d, J = 8.0 Hz, 2H); 7.48 (t, J = 7.5 Hz, 1H); from 7.53 to 7.63 (m, 3H); from 7.65 to 7.76 (m, 3H); 7.81 (broad d, J = 8.0 Hz, 1H); 8.34 (broad d, J = 8.0 Hz, 2H); 8.65 (s, 1H); 9.00 (broad s, 1H). IR spectrum (KBr): 3386; 1645; 1600; 1542; 1490; 1264; 1224; 901; 781; 719 and 691 cm$^{-1}$. Mass spectrum (ES): m/z = 329 [M + H]$^+$ (base peak). |
| 40 | $^1$H NMR spectrum (DMSO-d6, δ in ppm): 4.57 (d, J = 5.5 Hz, 2H); 5.25 (broad t, J = 5.5 Hz, 1H); 7.47 (d, J = 8.5 Hz, 2H); 7.59 (broad t, J = 7.5 Hz, 2H); from 7.65 to 7.72 (m, 3H); 7.75 (dd, J = 2.0 and 9.5 Hz, 1H); 7.81 (broad d, J = 9.5 Hz, 1H); 8.34 (broad d, J = 8.0 Hz, 2H); 8.63 (s, 1H); 8.99 (broad s, 1H). IR spectrum (KBr): 3377; 1642; 1635; 1596; 1542; 1512; 1258; 1206; 1037; 1022; 1005; 896; 796 and 722 cm$^{-1}$ Mass spectrum (ES): m/z = 329 [M + H]$^+$ (base peak) |
| 41 | $^1$H NMR spectrum (DMSO-d6, δ in ppm): 4.48 (d, J = 5.5 Hz, 2H); 5.23 (broad t, J = 5.5 Hz, 1H); from 7.32 to 7.50 (m, 4H); from 7.55 to 7.63 (m, 3H); 7.69 (broad t, J = 7.5 Hz, 1H); 7.76 (d, J = 9.5 Hz, 1H); 8.34 (broad d, J = 8.0 Hz, 2H); 8.64 (s, 1H); 8.66 (broad s, 1H). IR spectrum (KBr): 3407; 1644; 1543; 1266; 1018; 756 and 720 cm$^{-1}$ Mass spectrum (ES): m/z = 329 [M + H]$^+$ (base peak). |
| 42 | $^1$H NMR spectrum (DMSO-d6, δ in ppm): 7.60 (broad t, J = 7.5 Hz, 2H); 7.69 (broad t, J = 7.5 Hz, 1H); 7.78 (t, J = 7.5 Hz, 1H); from 7.81 to 7.88 (m, 2H); 7.98 (broad d, J = 7.5 Hz, 1H); 8.10 (broad d, J = 8.0 Hz, 1H); 8.28 (broad s, 1H); 8.34 (broad d, J = 8.0 Hz, 2H); 8.66 (s, 1H); 9.13 (broad s, 1H); 10.1 (s, 1H). IR spectrum (KBr): 3162; 2829; 2743; 1695; 1642; 1629; 1598; 1542; 1485; 1268; 1224; 1010; 894; 793; 707 and 690 cm$^{-1}$ Mass spectrum (EI): m/z 326 [M$^{+\cdot}$]. |
| 43 | $^1$H NMR spectrum (DMSO-d6, δ in ppm): 2.34 (s, 3H); 2.62 (s, 3H); 7.28 (d, J = 9.5 Hz, 1H); 7.53 (d, J = 9.5 Hz, 1H); 7.57 (broad t, J = 7.5 Hz, 2H); 7.67 (broad t, J = 7.5 Hz, 1H); 8.35 (broad d, J = 8.0 Hz, 2H); 8.47 (s, 1H). Mass spectrum (EI): m/z 250 (base peak): [M$^{+\cdot}$], m/z 221: [M − CO]$^+$. |

The compounds according to the invention underwent pharmacological tests to determine their modulatory effect on NOT.

Evaluation of the in vitro Activity on N2A Cells

The tests consisted in evaluating the in vitro activity of the compounds of the invention on a cell line (N2A) endogenously expressing the murine Nurr1 receptor and stably transfected with the NOT binding response element (NBRE) coupled to the luciferase reporter gene. The EC$_{50}$ values are between 0.01 and 1000 nM. The tests were performed according to the procedure described hereinbelow.

The cell line Neuro-2A is obtained from a standard commercial source (ATCC). The clone Neuro-2A was obtained from a spontaneous tumor originating from a strain of albino mice A by R. J Klebe et al. This line Neuro-2A is then stably transfected with 8NBRE-luciferase. The N2A-8NBRE cells are cultured to the point of confluence in 75 cm$^2$ culture flasks containing DMEM supplemented with 10% fetal calf serum, 4.5 g/L of glucose and 0.4 mg/ml of geneticin. After culturing for one week, the cells are recovered with 0.25% trypsin for 30 seconds and then resuspended in DMEM without phenol red, containing 4.5 g/L of glucose and 10% Hyclone defatted serum, and placed in white, transparent-based 96-well plates. The cells are deposited at a rate of 60 000 per well in 75 μL for 24 hours before adding the products. The products are applied in 25 μL and incubated for a further 24 hours. On the day of measurement, an equivalent volume (100 μL) of Steadylite is added to each well, and the wells are then left for 30 minutes to obtain complete lysis of the cells and maximum production of the signal. The plates are then measured in a microplate luminescence counter, after having been sealed with an adhesive film. The products are prepared in the form of a 10$^{-2}$ M stock solution, and then diluted in 100% of DMSO. Each concentration of product is prediluted in culture medium before incubation with the cells thus containing 0.625% final of DMSO.

For example, compounds 1, 3 and 6 gave an EC$_{50}$ value of 0.3 nM, 0.2 nM and 0.02 nM, respectively.

Evaluation of the Binding to the Human NOT Receptor

The direct binding between compounds of the invention and the human NOT receptor was evaluated using the SPR (surface plasmon resonance) technique. In this test, the protein is immobilized covalently on the matrix and the test molecule is injected into the chamber containing the sensor chip. The signal is directly proportional to the amount of product bound to the protein. The binding tests were performed in a Biacore S51 machine (Biacore Inc., Piscataway N.J.). The entire GST-NOT protein (NOT-FL) was supplied by Invitrogen (PV3265). The domain for binding to the NOT ligand (His-Thr-NOT 329-598) was expressed and purified as described in *Nature* 423, 555-560. The two proteins, diluted to a concentration of 20 μg/ml in pH 5.0 acetate buffer containing 5 mM of DTT, were immobilized on a surface of carboxymethyl 5' dextran (CM5 sensor chip, Biacore Inc.) via amine coupling according to the protocol recommended by Biacore, eluting with an HBS-N buffer (10 mM HEPES, 0.15 M NaCl, 3 mM EDTA, pH 7.4). Approximately 10 000-15 000 resonance units (RU) of the proteins are captured on the surface of the sensor chip CM5. The stock solutions of the test compounds at 1.5 mM in DMSO are serially diluted in elution buffer (50 mM HEPES pH 8; 150 mM NaCl; 10 mM MgCl$_2$; 2% DMSO, 1 mM DTT) at concentrations ranging from 3.75 to 0.1 μM. Each concentration of product is injected at 4° C. for 1 minute at 30 μl/min. The dissociation was recorded for 5 minutes without any other surface regeneration procedure. The signals obtained are corrected by testing each concentration of product on a surface of unmodified dextran (blank). The signal due to the migration buffer product is subtracted from the total signal ("double referencing"), as is the effect of the DMSO. Analysis of the signals was performed using the Biacore S51 analysis software (version 1.2.1). The compounds are then classified as a function of their maximum binding level and of kinetic parameters of binding to the immobilized protein.

By way of example, compounds 1 and 3 showed moderate affinity.

It is thus seen that the compounds according to the invention have a modulatory effect on NOT.

The compounds according to the invention may thus be used for the preparation of medicaments for their therapeutic application in the treatment or prevention of diseases involving the NOT receptors.

Thus, according to another of its aspects, a subject of the invention is medicaments comprising a compound of formula (I), or an addition salt thereof with a pharmaceutically acceptable acid.

These medicaments find their therapeutic use especially in the treatment and prevention of neurodegenerative diseases, for instance Parkinson's disease, Alzheimer's disease, tauopathies (e.g. progressive supranuclear palsy, frontotemporal dementia, corticobasal degeneration, Pick's disease); multiple sclerosis; cerebral trauma, for instance ischemia and cranial trauma and epilepsy; psychiatric diseases, for instance schizophrenia, depression, substance dependency, and attention-deficit hyperactivity disorder; inflammatory diseases, for instance vascular pathologies, atherosclerosis, joint inflammations, arthrosis, rheumatoid arthritis, osteoarthritis, and allergic inflammatory diseases such as asthma, and finally for the treatment of osteoporosis and cancers.

These compounds may also be used as a treatment combined with grafts and/or transplantations of stem cells.

According to another of its aspects, the present invention relates to pharmaceutical compositions comprising, as active principle, a compound according to the invention. These pharmaceutical compositions contain an effective dose of at least one compound according to the invention, or a pharmaceutically acceptable salt of said compound, and also at least one pharmaceutically acceptable excipient.

Said excipients are chosen, according to the pharmaceutical form and the desired mode of administration, from the usual excipients known to those skilled in the art.

In the pharmaceutical compositions of the present invention for oral, sublingual, subcutaneous, intramuscular, intravenous, topical, local, intratracheal, intranasal, transdermal or rectal administration, the active principle of formula (I) above, or the salt thereof, may be administered in unit administration form, as a mixture with standard pharmaceutical excipients, to man and animals for the prophylaxis or treatment of the above complaints or diseases.

The appropriate unit forms of administration include oral forms such as tablets, soft or hard gel capsules, powders, granules and oral solutions or suspensions, sublingual, buccal, intratracheal, intraocular, intranasal or inhalation administration forms, topical, transdermal, subcutaneous, intramuscular or intravenous administration forms, rectal administration forms and implants. For topical application, the compounds according to the invention may be used in creams, gels, ointments or lotions.

By way of example, a unit administration form of a compound according to the invention in tablet form may comprise the following components:

| | |
|---|---:|
| Compound according to the invention | 50.0 mg |
| Mannitol | 223.75 mg |
| Croscarmellose sodium | 6.0 mg |
| Corn starch | 15.0 mg |
| Hydroxypropylmethylcellulose | 2.25 mg |
| Magnesium stearate | 3.0 mg |

There may be particular cases in which higher or lower dosages are appropriate; such dosages are not outside the context of the invention. According to the usual practice, the dosage that is appropriate for each patient is determined by the doctor according to the mode of administration and the weight and Response of said patient.

According to another of its aspects, the present invention also relates to a method for treating the pathologies indicated above, which comprises the administration, to a patient, of an effective dose of a compound according to the invention, or a pharmaceutically acceptable salt thereof.

We claim:

1. A compound of formula (I):

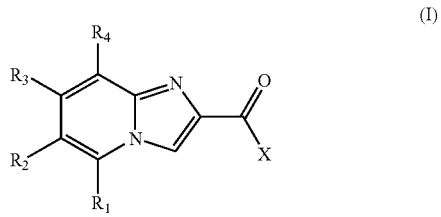

wherein:
X is phenyl optionally substituted with one or more groups chosen, independently of each other, from the group consisting of halogen, $(C_1\text{-}C_6)$alkoxy, $(C_1\text{-}C_6)$alkyl, $(C_3\text{-}C_7)$cycloalkyl$(C_1\text{-}C_6)$alkyl, $(C_3\text{-}C_7)$cycloalkyl$(C_1\text{-}C_6)$alkoxy, hydroxyl, amino and NRaRb;

$R_1$ is hydrogen, halogen, ($C_1$-$C_6$)alkoxy, ($C_1$-$C_6$)alkyl, ($C_3$-$C_7$)cycloalkyl($C_1$-$C_6$)alkyl, ($C_3$-$C_7$)cycloalkyl($C_1$-$C_6$)alkoxy, hydroxyl or amino, wherein the ($C_1$-$C_6$)alkyl group is optionally substituted with one or more times by halogen, hydroxyl, amino, or ($C_1$-$C_6$)alkoxy, and the ($C_1$-$C_6$)alkoxy group is optionally substituted with one or more times by halogen, hydroxyl, amino, or ($C_1$-$C_6$)alkoxy;

$R_2$ is ($C_1$-$C_6$)alkyl substituted with one or more groups chosen, independently of each other, from the group consisting of halogen, hydroxyl, amino and NRaRb, ($C_1$-$C_6$)alkoxy substituted with one or more groups chosen, independently of each other, from the group consisting of halogen, hydroxyl, amino and NRaRb, ($C_3$-$C_7$)cycloalkyl($C_1$-$C_6$)alkyl, ($C_3$-$C_7$)cycloalkyl($C_1$-$C_6$)alkoxy, ($C_2$-$C_6$)alkenyl, ($C_2$-$C_6$)alkynyl,

—CO—$R_5$,

—CO—$NR_6R_7$,

—CO—O—$R_8$,

—$NR_9$—CO—$R_{10}$, cyano, or phenyl optionally substituted with one or more groups chosen, independently of each other, from the group consisting of halogen, ($C_1$-$C_6$)alkoxy, ($C_1$-$C_6$)alkyl, ($C_3$-$C_7$)cycloalkyl($C_1$-$C_6$)alkyl, ($C_3$-$C_7$)cycloalkyl($C_1$-$C_6$)alkoxy, hydroxyl, amino, NraRb, and CO—$R_5$, wherein the ($C_1$-$C_6$)alkyl group is optionally substituted by hydroxyl group;

$R_3$ is hydrogen, ($C_1$-$C_6$)alkyl, halogen or hydroxyl;

$R_4$ is hydrogen or halogen;

$R_5$ is hydrogen or ($C_1$-$C_6$)alkyl;

$R_6$ and $R_7$ are, independently, hydrogen or ($C_1$-$C_6$)alkyl;

$R_8$ is ($C_1$-$C_6$)alkyl;

$R_9$ and $R_{10}$ are, independently, hydrogen or ($C_1$-$C_6$)alkyl;

$R_{11}$ is ($C_1$-$C_6$)alkyl;

$R_{12}$ is hydrogen or ($C_1$-$C_6$)alkyl;

Ra is ($C_1$-$C_6$)alkyl; and $R_b$ is hydrogen or ($C_1$-$C_6$)alkyl;

provided that:

at least one of $R_1$, $R_2$, $R_3$ and $R_4$ is not a hydrogen; and
the compound is not a compound of formula (I) wherein:

X is phenyl, $R_3$ is methyl, and $R_1$, $R_2$ and $R_4$ are hydrogen;

X is phenyl, $R_2$ is chlorine or methoxy, and $R_1$, $R_3$ and $R_4$ are hydrogen;

X is p-tolyl, $R_2$ is methyl, and $R_1$, $R_3$ and $R_4$ are hydrogen;

X is p-chlorophenyl, $R_1$ is chlorine, methoxy or methyl, and $R_2$, $R_3$ and $R_4$ are hydrogen;

X is p-chlorophenyl, $R_2$ is chlorine, and $R_1$, $R_3$ and $R_4$ are hydrogen;

X is p-chlorophenyl, $R_2$ is methyl, and $R_1$, $R_3$ and $R_4$ are hydrogen;

X is p-chlorophenyl, $R_4$ is methyl, and $R_1$, $R_2$ and $R_3$ are hydrogen;

X is p-chlorophenyl, $R_3$ is methyl, and $R_1$, $R_2$ and $R_4$ are hydrogen; or X is p-chlorophenyl, $R_1$ and $R_3$ are methyl, and $R_2$ and $R_4$ are hydrogen;

or an acid-addition salt thereof.

2. The compound according to claim 1, wherein $R_1$, $R_3$ and $R_4$ are hydrogen, or an acid-addition salt thereof.

3. The compound according to claim 1, wherein X is phenyl, or an acid-addition salt thereof.

4. The compound according to claim 1, which is:

Phenyl[6-(trifluoromethyl)imidazo[1,2-a]pyridin-2-yl]methanone or its hydrobromide (1:1);

[6-(1-Hydroxy-1-methylethyl)imidazo[1,2-a]pyridin-2-yl](phenyl)methanone or its hydrobromide (1:1);

[6-(Hydroxymethyl)imidazo[1,2-a]pyridin-2-yl](phenyl)methanone;

Phenyl(6-phenylimidazo[1,2-a]pyridin-2-yl)methanone;

N-(2-Benzoylimidazo[1,2-a]pyridin-6-yl)acetamide;

(6-Isopropenylimidazo[1,2-a]pyridin-2-yl)(phenyl)methanone;

2-Benzoyl-N,N-dimethylimidazo[1,2-a]pyridine-6-carboxamide;

2-Benzoyl-N-methylimidazo[1,2-a]pyridine-6-carboxamide;

Phenyl(6-vinylimidazo[1,2-a]pyridin-2-yl)methanone;

2-Benzoylimidazo[1,2-a]pyridine-6-carbonitrile;

2-Benzoylimidazo[1,2-a]pyridine-6-carboxamide;

2-benzoylimidazo[1,2-a]pyridine-6-carboxylate or its hydrobromide (1:1);

[6-(1-Ethoxypropyl)imidazo[1,2-a]pyridin-2-yl](phenyl)methanone;

1-(2-Benzoylimidazo[1,2-a]pyridin-6-yl)ethanone;

2-Benzoylimidazo[1,2-a]pyridine-6-carbaldehyde;

{6-[3-(Hydroxymethyl)phenyl]imidazo[1,2-a]pyridin-2-yl}(phenyl)methanone;

{6-[4-(Hydroxymethyl)phenyl]imidazo[1,2-a]pyridin-2-yl}(phenyl)methanone;

{6-[2-(Hydroxymethyl)phenyl]imidazo[1,2-a]pyridin-2-yl}(phenyl)methanone; or 3-(2-Benzoylimidazo[1,2-a]pyridin-6-yl)benzaldehyde;

or an acid-addition salt thereof.

5. A pharmaceutical composition comprising the compound according to claim 1 or an additional salt with a pharmaceutically acceptable acid, in combination with one or more pharmaceutically acceptable excipient.

6. A pharmaceutical composition comprising the compound according to claim 2 or an additional salt with a pharmaceutically acceptable acid, in combination with one or more pharmaceutically acceptable excipient.

7. A pharmaceutical composition comprising the compound according to claim 3 or an additional salt with a pharmaceutically acceptable acid, in combination with one or more pharmaceutically acceptable excipient.

8. A pharmaceutical composition comprising the compound according to claim 4 or an additional salt with a pharmaceutically acceptable acid, in combination with one or more pharmaceutically acceptable excipient.

* * * * *